US012629401B2

(12) United States Patent
Zou et al.

(10) Patent No.: US 12,629,401 B2
(45) Date of Patent: May 19, 2026

(54) METHOD FOR PREPARING GINSENG EXTRACT ENRICHED WITH RARE GINSENOSIDES AND APPLICATIONS THEREOF

(71) Applicants: Chenland Nutritionals Inc., Irvine, CA (US); Qingdao Marine Energizing Biotechnology Development Co., Ltd., Qingdao (CN)

(72) Inventors: Shengcan Zou, Qingdao (CN); Dongli Yin, Qingdao (CN); Jinli Chen, Qingdao (CN); Jinli Liu, Qingdao (CN); Decui Yin, Qingdao (CN); Haijun Zhang, Qingdao (CN)

(73) Assignees: Chenland Nutritionals Inc., Irvine, CA (US); Qingdao Marine Energizing Biotechnology Development Co., Ltd., Qingdao (CN)

( * ) Notice: Subject to any disclaimer, the term of this patent is extended or adjusted under 35 U.S.C. 154(b) by 256 days.

(21) Appl. No.: 18/544,500

(22) Filed: Dec. 19, 2023

(65) Prior Publication Data

US 2024/0115640 A1 Apr. 11, 2024

(30) Foreign Application Priority Data

Aug. 26, 2023 (CN) .......................... 202311087230.1

(51) Int. Cl.
| | |
|---|---|
| A61K 36/258 | (2006.01) |
| A61K 36/076 | (2006.01) |
| A61K 36/64 | (2006.01) |
| A61P 39/06 | (2006.01) |

(52) U.S. Cl.
CPC .......... *A61K 36/258* (2013.01); *A61K 36/076* (2013.01); *A61K 36/64* (2013.01); *A61P 39/06* (2018.01); *A61K 2236/331* (2013.01); *A61K 2236/333* (2013.01); *A61K 2236/51* (2013.01)

(58) Field of Classification Search
None
See application file for complete search history.

(56) References Cited

U.S. PATENT DOCUMENTS

| | | |
|---|---|---|
| 2005/0031711 A1 | 2/2005 | Park |
| 2006/0228430 A1 | 10/2006 | Jung et al. |
| 2011/0268823 A1 | 11/2011 | Kim et al. |

OTHER PUBLICATIONS

"Enrich" definition (https://www.merriam-webster.com/dictionary/enrich—accessed Feb. 2026).*
Kim (KR 20080067076 A—English translation)—Jul. 18, 2008.*

* cited by examiner

*Primary Examiner* — Susan Hoffman
(74) *Attorney, Agent, or Firm* — Hemisphere Law, PLLC

(57) ABSTRACT

A method for preparing ginseng extract rich in rare ginsenosides is disclosed. Ginseng roots or ginseng stems and leaves are extracted, enzymatically hydrolyzed and treated with high temperature and high pressure. The preparation method can quickly and effectively increase the proportion of rare ginsenosides in the ginseng extract. After in vitro antioxidant experiments and in vivo experiments with *Hidradenitis elegans* nematode, the extract and related complexes were proved to be effective in antioxidant, anti-oxidative stress, and improving age-related muscle decline and other dysfunctions. After genetic and metabolomic studies, the anti-aging mechanism was proved to be related to the expression of genes associated with nutrient sensing, stress-related pathways and redox processes, and showed innate immune response and redox process GO enrichment, proving its oxidative stress resistance.

6 Claims, 14 Drawing Sheets

METHOD FOR PREPARING GINSENG EXTRACT ENRICHED WITH RARE GINSENOSIDES AND APPLICATIONS THEREOF

TECHNICAL FIELD

The present invention relates to the technical field of ginsenoside extraction, and more specifically to a method of preparing a ginseng extract enriched with rare ginsenosides and its application.

BACKGROUND

Ginseng, as a traditional Chinese medicine in China, has been used for more than 2000 years and is known as the "king of all herbs", and has been widely used worldwide thanks to its unique pharmacological activity. Ginsenoside is the main active substance in ginseng, which has unique biological activity and medicinal value. The biological activities of ginsenosides include anti-cancer, anti-aging, anti-inflammatory, anti-allergic, anti-diabetic, anti-hyperlipidemic, anti-fatigue and antioxidant activities, and they can also promote the synthesis of DNA, RNA and protein.

Ginsenoside is an important active ingredient of ginseng and belongs to triterpenoid glycoside compounds, which can be categorized into protopanaxadiol group saponins (PPD-type saponins), protopanaxatriol group saponins (PPT-type saponins), and oleanocarpane type. Literature studies have shown that more than 100 ginsenosides have been isolated and identified from traditional Chinese medicines such as ginseng or *Panax ginseng*, among which ginsenosides Rb1, Rb2, Rc, Rd, Re, Rf and Rg1 account for more than 90% of the total ginsenosides, and they are usually regarded as the major ginsenosides. The poor water solubility, low blood concentration, slow oral absorption and low bioavailability of ginsenosides limit the clinical application of ginsenosides to some extent.

Studies have shown that structural modification of ginsenosides by acylation, sulfation, PEG modification, amino acid, oxidation, nitrogen hybridization, alkylation, deuterated reduction, etc., can effectively improve the water solubility, stability, targeting, and thus bioavailability of ginsenosides, and significantly improve the drug activity of ginsenosides. However, the structural modification of ginsenoside molecules by the above methods leads to the problems such as organic solvent residue, which is not favorable for the clinical application in the later stage.

It has been found that the secondary metabolite of ginsenoside after conversion has stronger biological activity, and this secondary metabolite is called rare ginsenoside. The content of rare ginsenosides in ginseng is very small, and the absorption of the main ginsenosides in the human gastrointestinal tract is very poor, while rare ginsenosides are more easily absorbed by the human body and play a role. It has been proved that rare ginsenosides have better pharmacological activities and are potential drug candidates for cancer treatment. Currently, the low yield of rare ginsenosides extracted from ginseng and other traditional Chinese medicines cannot meet the market demand, which limits their development and application, therefore, it is of great importance to prepare rare ginsenosides by converting major ginsenosides. Physical and chemical methods are not suitable for industrialized large-scale production of ginsenosides, such as acid hydrolysis method can produce rare ginsenosides, but the reaction process is violent, and the conversion rate of rare ginsenosides is not high; alkaline hydrolysis method to obtain rare ginsenosides is very demanding on the conditions of pH, pressure and temperature; microbial conversion method to obtain rare ginsenosides has the advantages of fast, convenient, effective and harmless, but the equipment requirements are high, and the process is relatively complex. The microbial transformation method has the advantages of rapid, convenient, effective and harmless, but the equipment requirements are high and the process is relatively complicated. Enzymatic hydrolysis has high specificity and is considered to be one of the most effective ways to prepare rare ginsenosides, but the yield is generally not high, and the current research focuses on the biocatalysis of single ginsenosides, and there is a waste of the refining process, and there are fewer cases of conversion of ordinary ginseng extracts into rare ginsenosides. As Chinese medicine focuses on the holistic concept, there is an urgent need for a method to utilize ginseng extracts in a high-value way.

Therefore, for those skilled in the art, a method of preparing a ginseng extract enriched with rare ginsenosides and its application requires to be provided.

SUMMARY

In view of this, the present invention provides a method of preparing a ginseng extract enriched with rare ginsenosides and its application.

In order to realize the above purposes, the present invention adopts the following technical solutions:

A method for the preparation of ginseng extract rich in rare ginsenosides, prepared by the method of enzymatic hydrolysis and heat treatment, the specific steps are as follows:

(1) ginseng stems and leaves extract dry powder or ginseng roots extract dry powder was prepared with water to form a substrate at a concentration of 10-20% (w/v), and the pH was adjusted to 4.3-5.0;

(2) Add 2~5 U/g (U is the unit of enzyme activity, and/g refers to accounting on the basis of dry powder) of β-glucosidase for enzymatic hydrolysis at a temperature of 40~60° C. and an enzymatic hydrolysis time of 3~5 h in terms of the said dry powder; and carry out a heat treatment after the enzymatic hydrolysis at a temperature of 115~132° C., a pressure of 70~200 kPa for the heat treatment, and a heat treatment time of 1~4 h;

(3) The treated solution was concentrated at a concentration temperature of 75~85° C. and a concentration pressure of −0.05~−0.09 Mpa to a specific gravity of 1.1-1.2 g/L (25° C.) to obtain the concentrated solution;

(4) The concentrate obtained in step (3) was subjected to centrifugal spray drying with the following parameters: inlet air temperature 135-160° C., outlet air temperature 80-100° C., centrifugal frequency 250-280 Hz, induced air frequency 50-60 Hz, feed pump 10-40 RPM.

Preferably, a method of preparing a ginseng extract enriched with rare ginsenosides is performed as follows:

(1) ginseng stems and leaves extract dry powder or ginseng roots extract dry powder was prepared with water to form a substrate at a concentration of 15%, and the pH was adjusted to 4.5;

(2) Take the said dry powder, add 3 U/g β-glucosidase for enzymatic hydrolysis, the enzymatic hydrolysis temperature is 50° C., the enzymatic hydrolysis time is 4 h; after the enzymatic hydrolysis and heat treatment is carried out, the temperature of heat treatment is 115°

C., the pressure of heat treatment is 70 kPa, and the time of heat treatment is 2 h;

(3) The treated solution was concentrated at a concentration temperature of 77° C. and a concentration pressure of −0.08 MPa to a specific gravity of 1.15 g/L (25° C.) to obtain a concentrated solution;

(4) The concentrate obtained in step (3) was subjected to centrifugal spray drying with the following parameters: inlet air temperature 140° C., outlet air temperature 100° C., centrifugal frequency 280 Hz, induced air frequency 50 Hz and feed pump 20 RPM.

Further, the ginseng stems and leaves extract dry powder was prepared by ethanol extraction with an ethanol concentration of 70%, the extraction material-liquid ratio was 1:8, the number of extraction times was 2, and the extraction time was 2 hours each time, and the alcoholic extract was obtained; the alcoholic extract was concentrated, and the concentration temperature was 65° C., and the concentration pressure was −0.06 Mpa, and the concentration was concentrated until the specific gravity was 1.05 g/L (25° C.), and the concentrated liquid was obtained. The concentrate was subjected to centrifugal spray drying with the following parameters: inlet air temperature 140° C., outlet air temperature 100° C., centrifugal frequency 280 Hz, induced air frequency 50 Hz and feed pump 20 RPM.

Further, the ginseng roots extract dry powder is prepared by ethanol extraction with an ethanol concentration of 60%, extraction material-liquid ratio of 1:10, the number of extraction times is 3 times, each extraction time for 3 hours, to obtain alcohol extract; alcohol extract concentration, concentration temperature of 65° C., concentration pressure of −0.06 Mpa, concentration to the specific gravity of 1.05 g/L (25° C.), to obtain the concentrated solution. The concentrate was centrifugal spray dried with the following parameters: inlet air temperature 140° C., outlet air temperature 100° C., centrifugal frequency 280 Hz, induced air frequency 50 Hz, and feed pump 20 RPM.

Further, a ginseng stems and leaves extract enriched with rare ginsenosides is obtained by utilizing the preparation method described above; the proportion of rare ginsenosides in the ginseng stems and leaves extract is higher than or equal to 30%.

Further, a ginseng roots extract enriched with rare ginsenosides is obtained by utilizing the preparation method described above; the proportion of rare ginsenosides in the ginseng roots extract is higher than or equal to 15%.

Further, a formulation including the ginseng extract enriched with rare ginsenosides is prepared. The formulation includes, but is not limited to, any acceptable dosage form such as bulk, granules, tablets, capsules, softgels, gummies, oral liquids, and the like.

Further, the ginseng extract enriched with rare ginsenosides is used in the preparation of antioxidant, anti-stress and aging-induced muscle loss products.

Further, a composition including rare ginsenoside-rich ginseng extract, Poria extract, and radix rehmanniae extract is prepared. The substances combined with the rare ginsenoside-rich ginseng extract include, but are not limited to, Poria, radix rehmanniae, and other common Chinese medicine extracts.

Further, the compositions are applied in the preparation of antioxidant, anti-stress and aging-induced muscle decline products.

As can be seen from the above technical solution, compared with the prior art, the present invention discloses and provides a method of preparing a ginseng extract enriched with rare ginsenosides and its application, wherein the ginseng extract enriched with rare ginsenosides is obtained from ginseng roots or ginseng stems and leaves by extracting, enzymatically hydrolyzing and treating with high temperature and high pressure. The preparation method can rapidly and effectively increase the proportion of rare ginsenosides in the ginseng extract. After in vitro antioxidant experiments and in vivo experiments with *Cryptomeria japonica* nematode, it was proved that the extract and related complexes could effectively antioxidant, anti-oxidative stress and improve age-related muscle decline and other dysfunctions. After genetic and metabolomics studies, it was demonstrated that the anti-aging mechanism was related to the expression of genes associated with nutrient sensing, stress-related pathways and redox processes, and exhibited innate immune response and redox process GO enrichment, proving its oxidative stress resistance.

BRIEF DESCRIPTION OF THE DRAWINGS

In order to more clearly illustrate the technical solutions in the embodiments or prior art of the present invention, the accompanying drawings to be used in the description of the embodiments or prior art will be briefly introduced below, and it will be obvious that the accompanying drawings in the following description are only embodiments of the present invention, and or those ordinary skilled in the art, other drawings can be obtained in accordance with the accompanying drawings provided, without creative labor.

Figure 7:
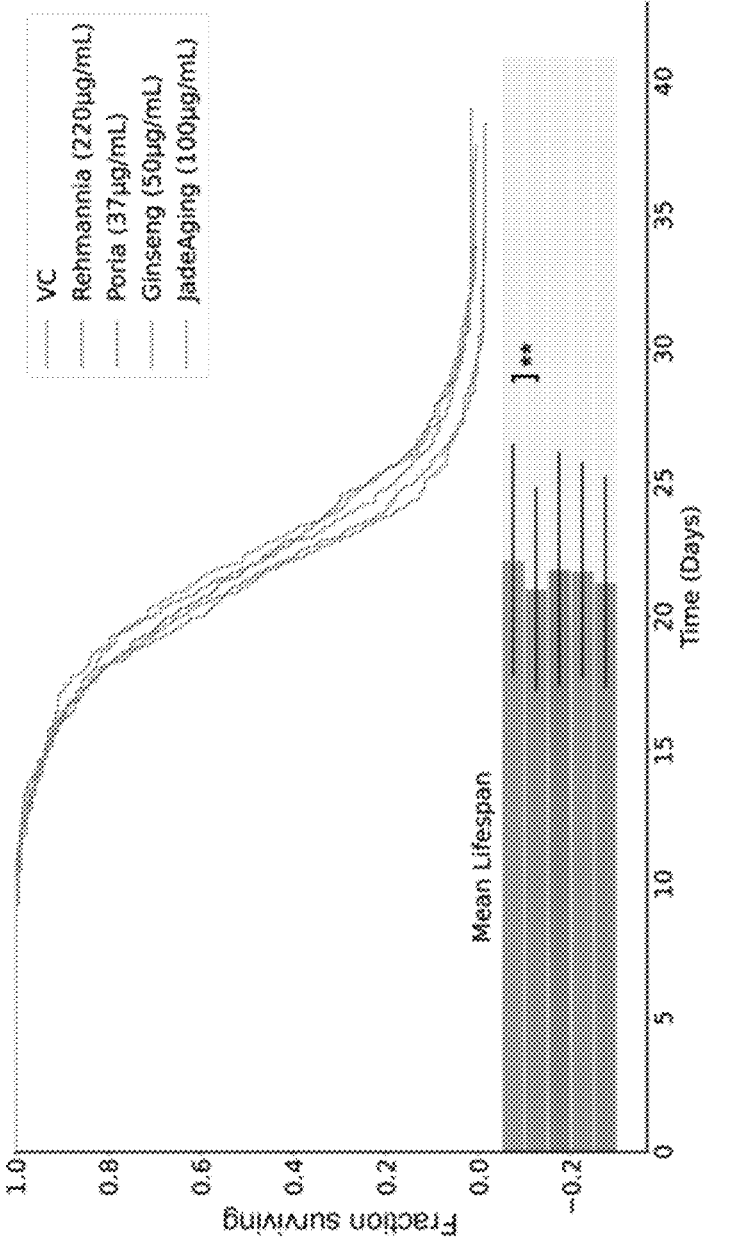
Figure 8:
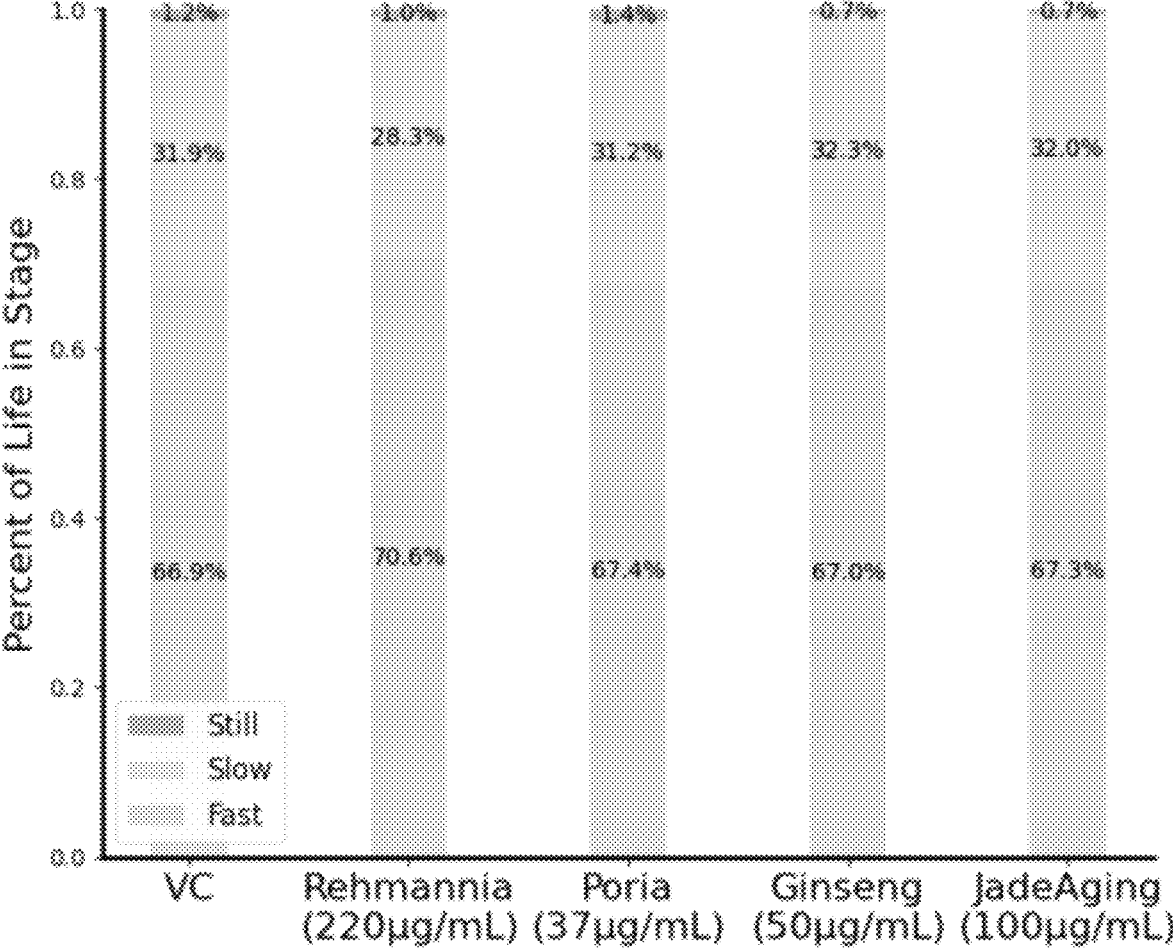
Figure 9:
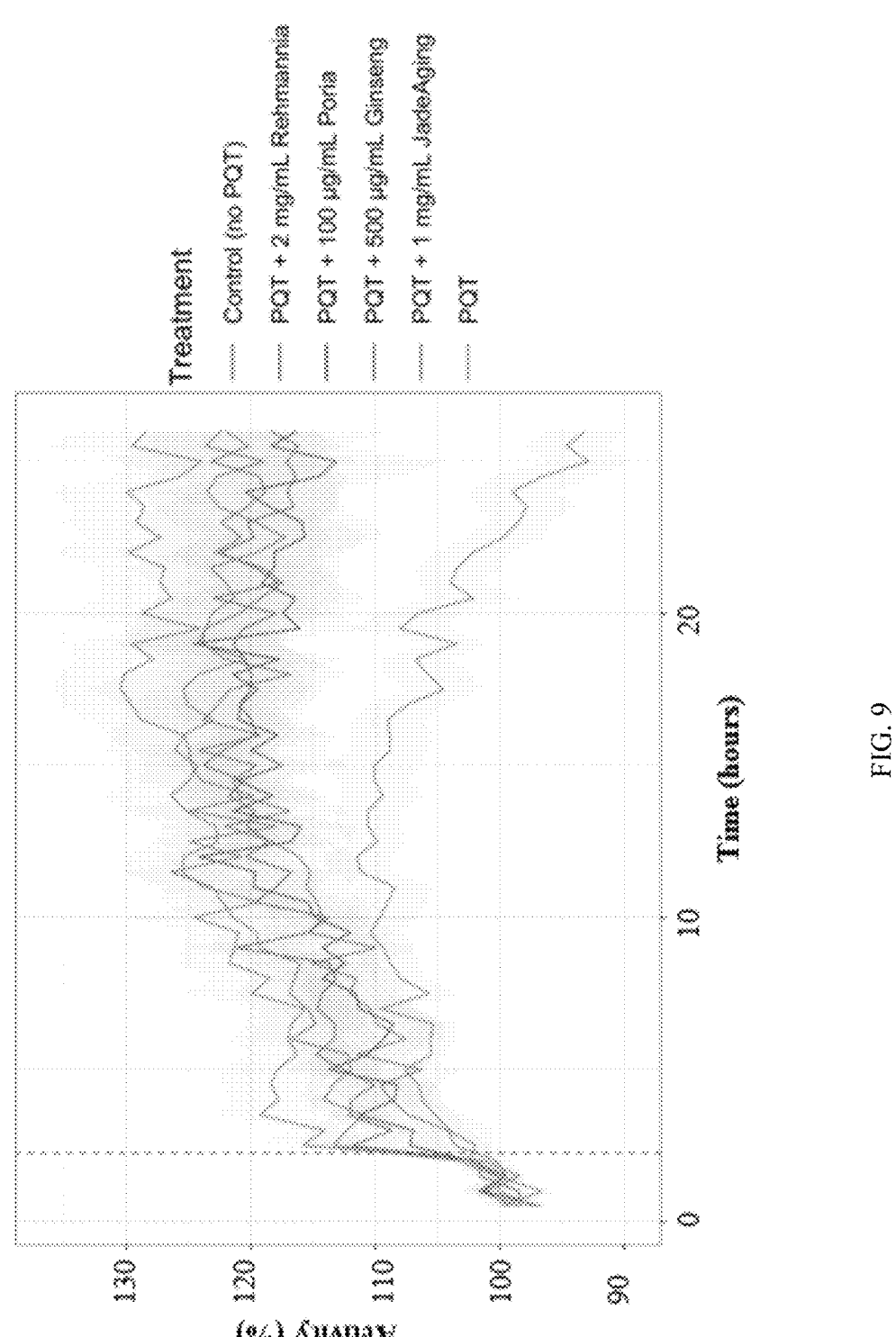
Figure 10:
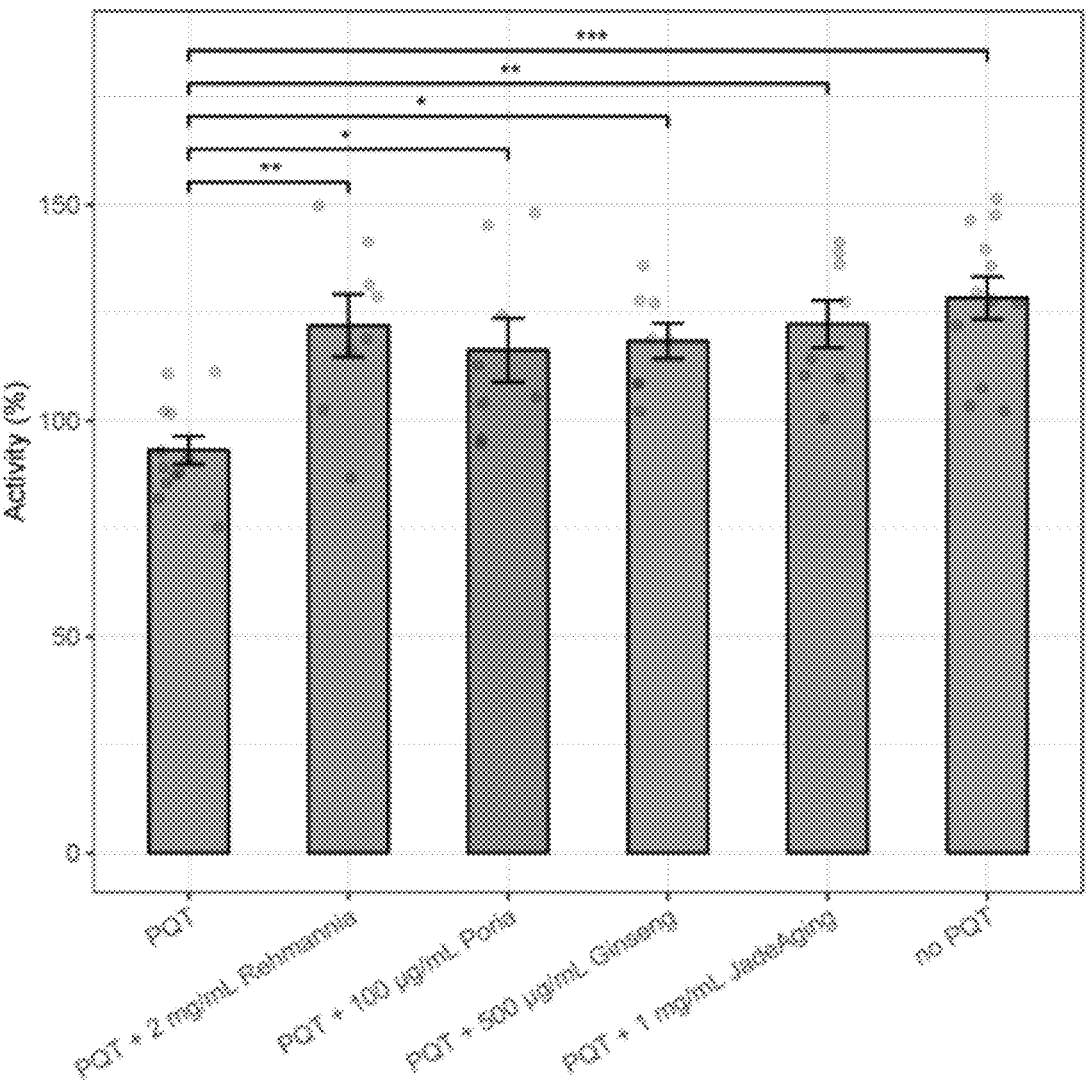
Figure 11:
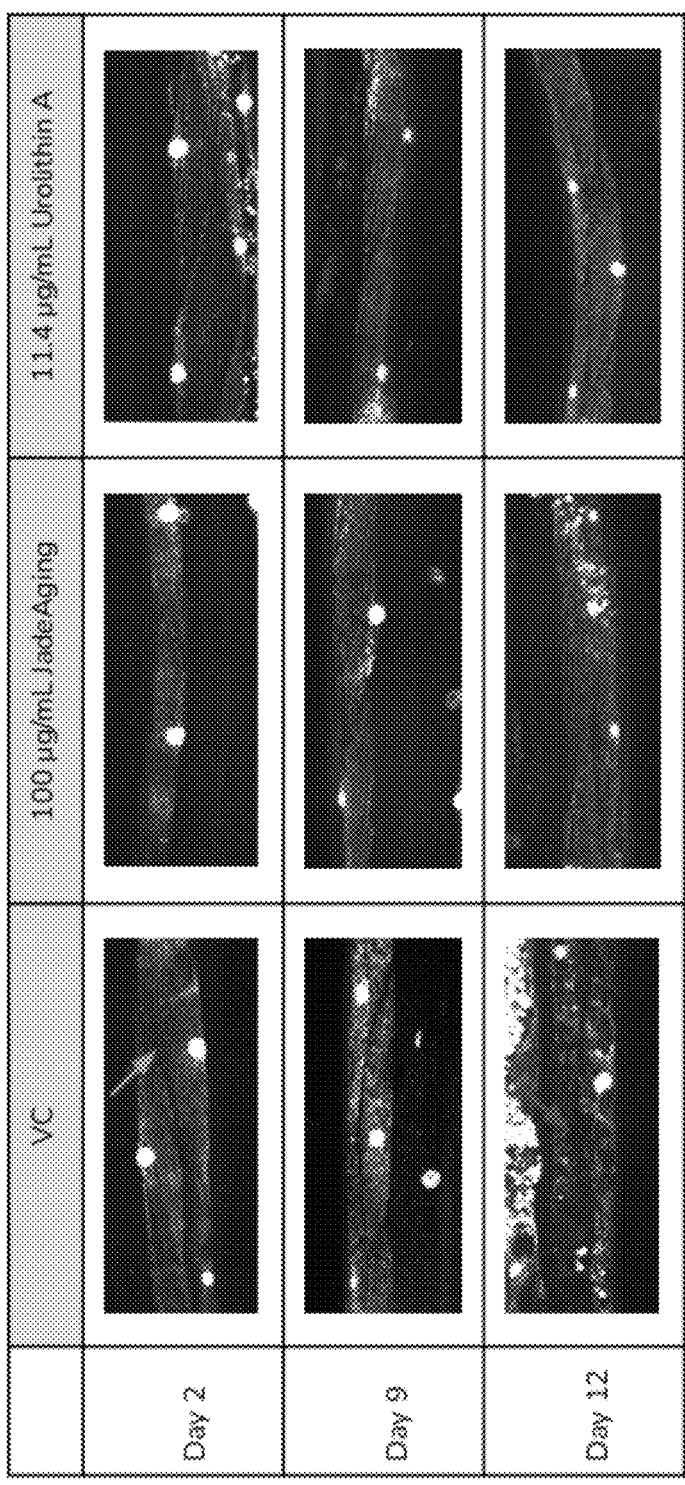
Figure 12:
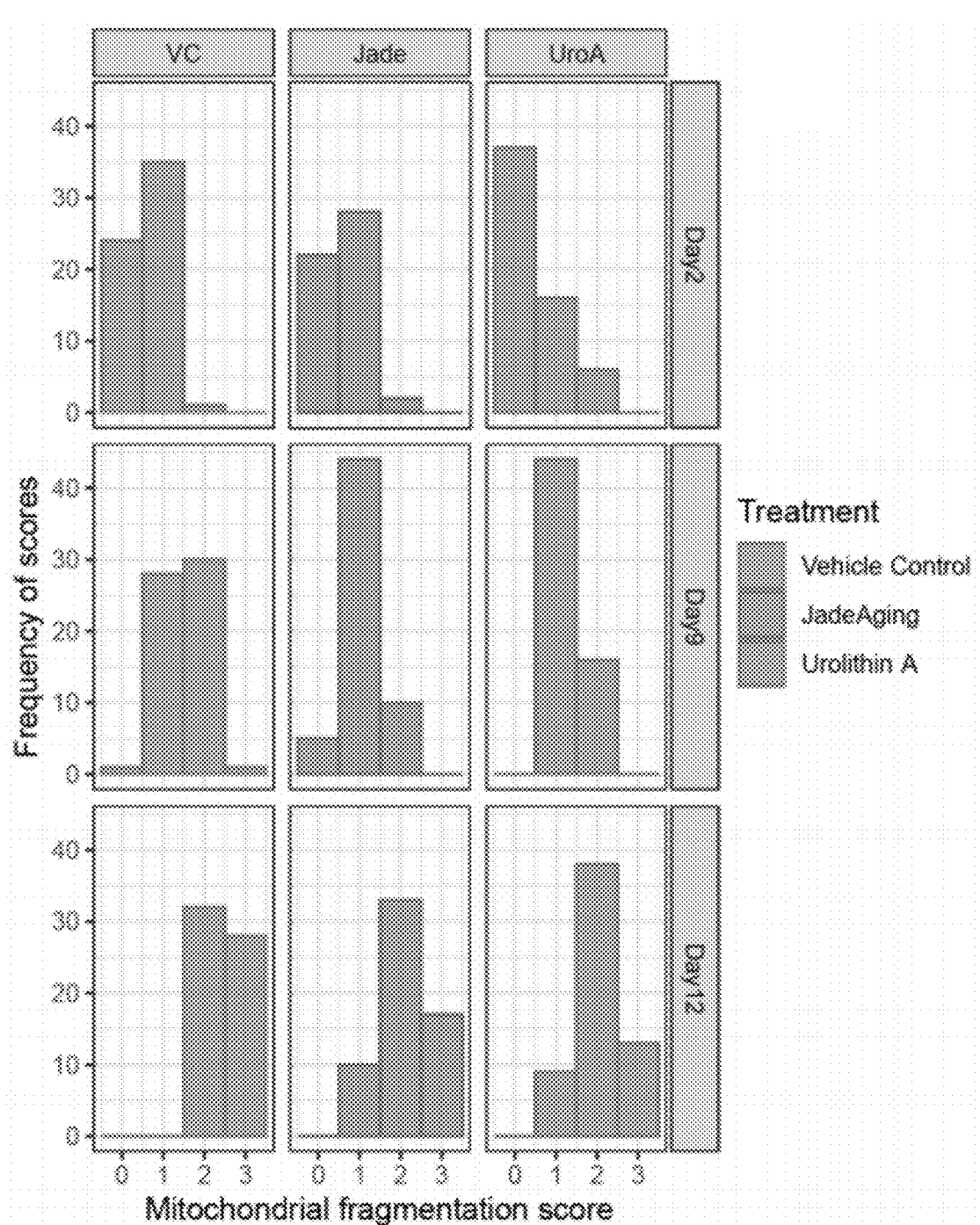
Figure 13:
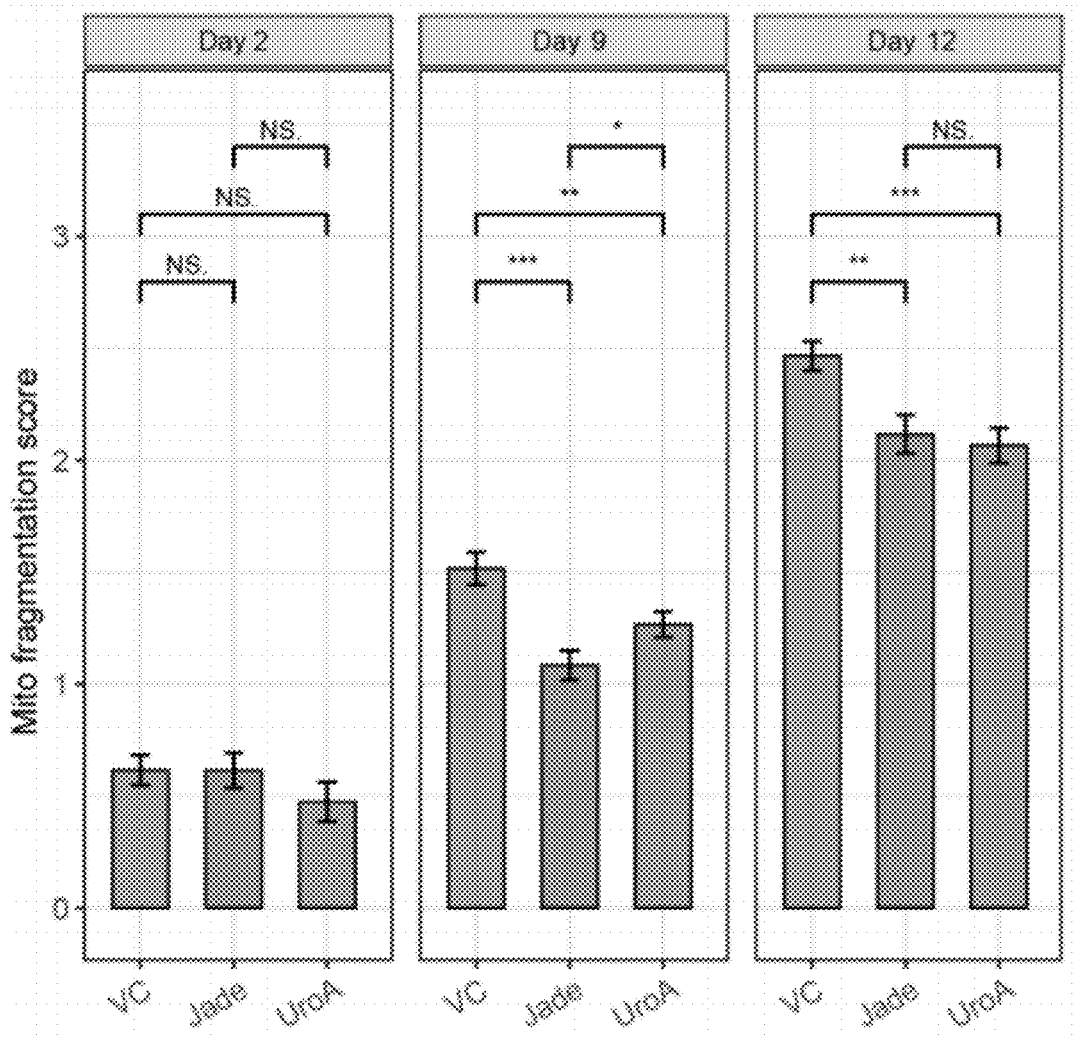
Figure 14:
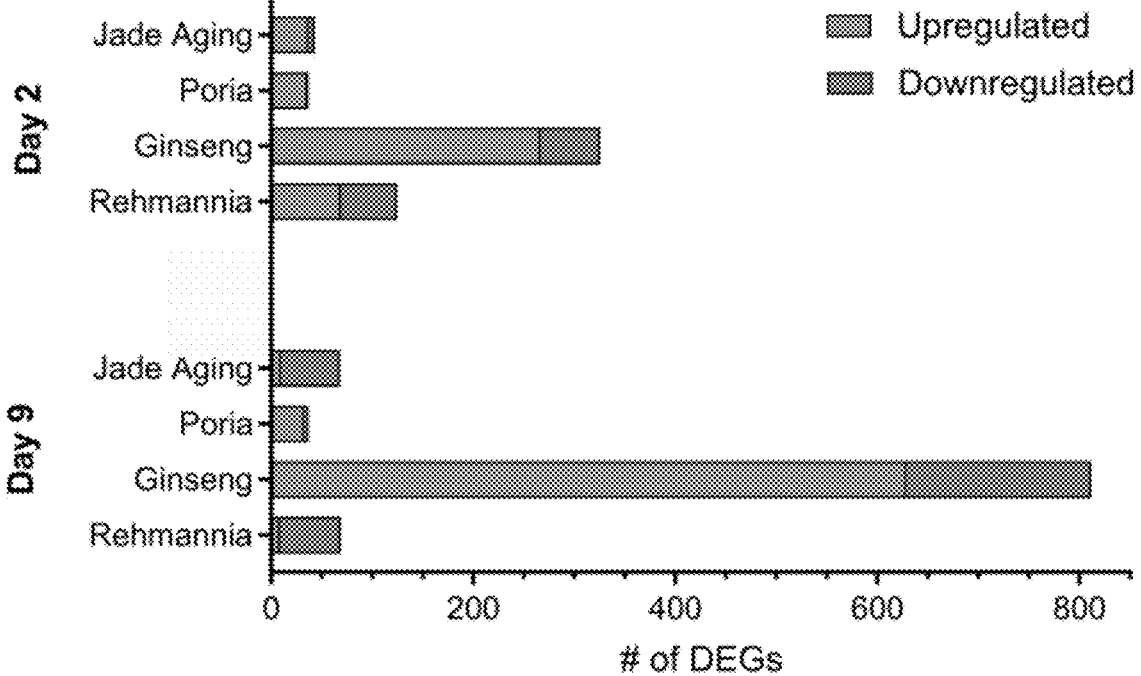

The dashed line identifies the average size of nematodes in the blank group (VC group) and the size is quantified as area; the box indicates the average area and the dots are individual animals; the error bars indicate the standard error of the mean (SEM); and the * indicates the reference concentration selected for further study;

FIG. 7 shows the life span test of the showy cryptic rod nematode of the present invention;

Wherein, the bars indicate the mean life expectancy in each case, the error bars indicate the standard deviation, and the means were compared using analysis of variance followed by post hoc t tests; *P<0.05; P<0.01; *P<0.001; ****P<0.0001;

FIG. 8 shows the state of activity during the life cycle of the showy cryptic rod nematode of the present invention;

FIG. 9 shows the motility of the showy cryptic rod nematode of the present invention after exposure to PQT; activity is normalized to the mean baseline and shading indicates the standard error of the mean;

FIG. 10 shows the motility of *Cryptobacterium hidradii* nematodes of the present invention after exposure to PQT for 24 h; *P<0.05; P<0.01; *P<0.001; ****P<0.0001;

groups were compared using ANOVA followed by post hoc t-tests corrected for multiple comparisons (Bonferroni);

FIG. 11 shows the muscle images of the group of samples to be tested at different ages of the present invention;

FIG. 12 shows the distribution of fragmentation scores for each age treatment group of the present invention;

FIG. 13 shows the mean fragmentation scores of the treatment groups for each age group of the present invention; *P<0.05; P<0.01; *P<0.001; ****P<0.0001. Comparisons of groups were made using analysis of variance (ANOVA) followed by post hoc t-tests;

FIG. 14 shows the number of differentially expressed genes in each treatment group of the present invention.

DETAILED DESCRIPTIONS

The technical solutions in the embodiments of the present invention will be described clearly and completely in the following in conjunction with the accompanying drawings in the embodiments of the present invention, and it is obvious that the described embodiments are only a part of the embodiments of the present invention and not all of the embodiments. Based on the embodiments of the present invention, all other embodiments obtained by a person of ordinary skill in the art without making creative labor are within the scope of protection of the present invention.

1, 1-diphenyl-2-picrylhydrazyl (DPPH), 2, 2'-azino-bis-3-ethylbenzothiazoline-6-sulfonic acid [2,2'-azino-bis(3-ethylbenzothiazoline-6-sulfonic acid), ABTS]: Beijing Qiyan Biotechnology Co. Ferrous sulfate, 30% hydrogen peroxide (all analytically pure): Tianjin Windship Chemical Reagent Technology Co. Tris-(hydroxymethyl)aminomethane hydrochloride (Tris-HCl), Vc, o-diazafil (all analytically pure): Sinopharm Chemical Reagent Co. o-Benzenetriol (analytically pure): Tianjin Fuchen Chemical Reagent Factory.

Embodiment I. Preparation of Ginseng Extract Rich in Rare Ginsenosides by Enzymatic Hydrolysis and Heat Treatment 1) Preparation of Ginseng Stems and Leaves Extract Dry Powder and Ginseng Roots Extract Dry Powder (1) ginseng stems and leaves extract dry powder (homemade, batch No. RSY230201) preparation method: dried ginseng stems and leaves were extracted by ethanol with an ethanol concentration of 70%. The extraction material-liquid ratio is 1:8, the number of extraction is 2 times, and each extraction time is 2 hours. The concentration temperature of the alcohol extract was 65° C., the concentration pressure was −0.06 Mpa, and it was concentrated to the specific gravity of 1.05 (25° C.). The concentrate was subjected to centrifugal spray drying with the following parameters: inlet air temperature of 140° C., outlet air temperature of 100° C., centrifugal frequency of 280 Hz, induced air frequency of 50 Hz, and feed pump of 20 RPM.

(2) ginseng roots extract dry powder (homemade, batch number RSG230201) preparation method: dried ginseng roots were extracted by ethanol with an ethanol concentration of 60%. The extraction material-liquid ratio is 1:10, the number of extraction is 3 times, and each extraction time is 3 hours. The concentration temperature of the alcohol extract was 65° C., the concentration pressure was −0.06 Mpa, and it was concentrated to the specific gravity of 1.05 (25° C.).

The concentrate was subjected to centrifugal spray drying with the following parameters: inlet air temperature of 140° C., outlet air temperature of 100° C., centrifugal frequency of 280 Hz, induced air frequency of 50 Hz, and feed pump of 20 RPM.

2) Enzymatic Plus Heat Treatment Preparation Process (1) Batch No. XRSY230301: ginseng stems and leaves extract dry powder (homemade, Batch No. RSY230201) was prepared with water to form a 15% concentration of the substrate, adjusted pH to 4.5, and added with 3 U/g of β-glucosidase. The enzymatic hydrolysis temperature was 50° C., the time of enzymatic hydrolysis was 4 h, and the temperature of heat treatment was 115° C. The pressure of heat treatment was 70 kPa, and the time of heat treatment was 2 h.

(2) Batch No. XRSG230301: ginseng roots extract dry powder (homemade, batch No. RSG230201) was prepared with water to form a 15% concentration of the substrate, adjusted the pH to 4.5, and added with 3 U/g of β-glucosidase, with the enzymatic hydrolysis temperature at 50° C. and the enzymatic hydrolysis time of 4 h, and the heat-treatment temperature at 115° C., the heat-treatment pressure at 70 kPa, and the heat-treatment time of 2 h.

(3) Batch No. XRSY230302: ginseng stems and leaves extract dry powder (Hanzhong Natural Valley Biotechnology Co., Ltd., Batch No. Crs230310) was prepared with water to form a 15% concentration of the substrate, adjusted the pH to 4.5, and added with 3 U/g of β-glucosidase, with the enzymatic hydrolysis temperature at 50° C. and the time of enzymatic hydrolysis of 4 h, and the temperature of heat treatment at 115° C., and the pressure of heat treatment at 70 kPa. The heat treatment time was 2 h.

(4) Batch No. XRSG230302: ginseng root extract dry powder (Hongjiu Biotechnology Co., Ltd, Batch No. S220406) was prepared with water to form a 15% concentration of the substrate, adjusted the pH to 4.5, and added with 3 U/g of β-glucosidase, with the enzymatic hydrolysis temperature at 50° C. and the time of enzymatic hydrolysis of 4 h, and the temperature of heat treatment at 115° C., the pressure of heat treatment at 70 kPa, and the time of heat treatment of 2 h.

The extracts obtained from the above (1)-(4) "Enzymatic hydrolysis plus heat treatment" were concentrated at 77° C., concentration pressure −0.08 Mpa, and concentrated to a specific gravity of 1.15 (25° C.). The concentrate was spray dried by centrifugal type with the following parameters: inlet temperature 140° C., outlet temperature 100° C., centrifugal frequency 280 Hz, induced air frequency 50 Hz, feed pump 20 RPM, i.e. the extract powder rich in rare ginseng saponins was obtained.

(3) Physicochemical Indexes of Spray-Dried Products (Extract Powder Rich in Rare Ginsenosides) were Tested.

Among them, the results of yield, particle size, moisture and ash are shown in Table 1.

TABLE 1

| Physical and chemical indexes of spray-dried products-1 | | | | |
|---|---|---|---|---|
| batch number | Yield | Particle size (80 mesh sieve) | Padding | Ash |
| XRSY230301 | 90.52% | 98.02% | 1.90% | 0.39% |
| XRSY230302 | 91.02% | 97.65% | 1.86% | 0.38% |

TABLE 1-continued

Physical and chemical indexes of spray-dried products-1

| batch number | Yield | Particle size (80 mesh sieve) | Padding | Ash |
|---|---|---|---|---|
| XRSG230301 | 90.10% | 98.21% | 2.05% | 0.40% |
| XRSG230302 | 89.65% | 99.01% | 1.95% | 0.39% |

Note:

Yield: weight of dry powder obtained after "enzymatic hydrolysis + heat treatment"/weight of dry powder of ginseng extract before treatment * 100%;

Particle size (after 80 mesh sieve): weight of dry powder after 80 mesh sieve/total dry powder before sieve * 100%;

Ash: Ash refers to the inorganic matter that remains after the sample is scorched at high temperature. It is carried out in accordance with GB 5009.4-2016 National Standard for Food Safety Determination of Ash in Food.

The fingerprints of the obtained extract powder enriched with rare ginsenosides were detected by high performance liquid chromatography (HPLC), and the chromatographic conditions were as follows: the chromatographic column was C18, specification: 4.6×300 mm, 5 μm; the column temperature was 30° C.; the flow rate was 1.3 mL/min; the detection wavelength was 202 nm; the mobile phase A was acetonitrile, and the mobile phase B was 0.1% phosphoric acid in water, and the gradient elution procedure The gradient elution program was:

| Time (minutes) | Mobile phase A (%) | Mobile phase B (%) |
|---|---|---|
| 0 | 19.0 | 81.0 |
| 30 | 19.0 | 81.0 |
| 35 | 24.0 | 76.0 |
| 60 | 40.0 | 60.0 |
| 90 | 55.0 | 45.0 |
| 100 | 60.0 | 40.0 |

-continued

| Time (minutes) | Mobile phase A (%) | Mobile phase B (%) |
|---|---|---|
| 105 | 19.0 | 81.0 |
| 115 | 19.0 | 81.0 |

Preparation of test solution: weigh 0.1 g of the sample in a 10 mL volumetric flask, add methanol, sonicate for 30 minutes, remove and cool to room temperature, dilute with methanol to the scale, shake, and then filter through a 0.22 μm membrane to obtain the solution.

The results of the extract powder enriched with rare ginsenosides are shown in Table 2.

Figure 1:
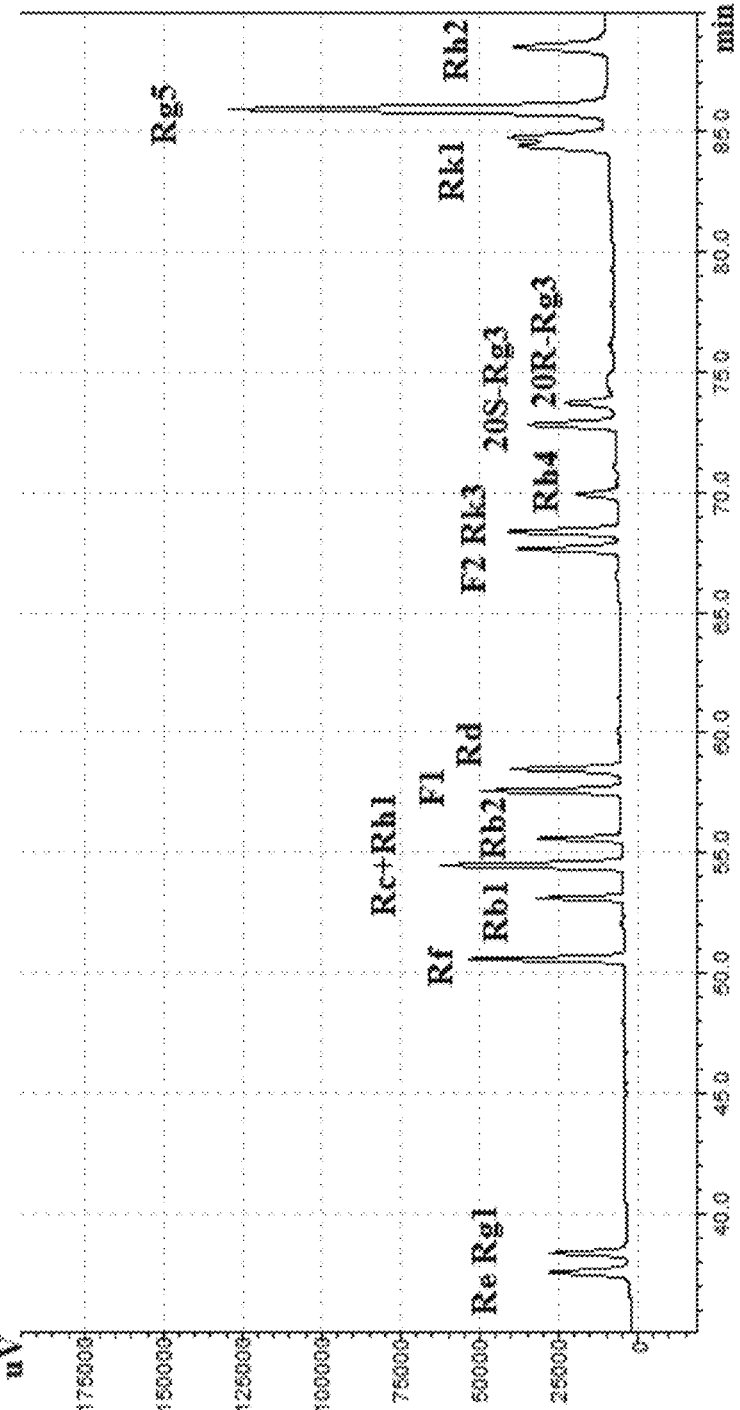
FIG. 1 is a chromatogram of the 17 standard ginsenosides of the present invention.

The chromatograms of 17 of these ginsenoside standards are shown in FIG. 1.

TABLE 2

Physicochemical indexes of spray-dried products-2

| Ginsenoside Standard | Content before treatment (%, g/100 g) | | | | Content after "enzymatic hydrolysis + heat treatment" (%, g/100 g) | | | |
|---|---|---|---|---|---|---|---|---|
| | RSY230201 | Crs230310 | RSG230201 | S220406 | XRSY230301 | XRSY230302 | XRSG230301 | XRSG230302 |
| Re | 3.53 | 1.27 | 0.84 | 1.34 | 0.52 | 0.69 | 0.72 | 0.74 |
| Rg1 | 10.64 | 3.02 | 2.2 | 2.22 | 0.99 | 1.6 | 1.61 | 1.46 |
| Rf | 0 | 0 | 0.4 | 0.51 | 0 | 0 | 0.34 | 0.4 |
| Rb1 | 2.72 | 0.47 | 3.05 | 2.92 | 0.46 | 0.27 | 2.56 | 2.38 |
| Rc + Rh1 | 1.83 | 0.33 | 2.08 | 2.2 | 1.4 | 0.29 | 2.69 | 2.85 |
| Rb2 | 2.63 | 0.49 | 2.98 | 2.33 | 2.56 | 0.52 | 2.97 | 2.44 |
| F1 | 1.05 | 0.36 | 0 | 0 | 0.52 | 0.22 | 0 | 0 |
| Rd | 3.18 | 0.99 | 1.04 | 1.82 | 2.5 | 0.92 | 0.75 | 1.76 |
| F2 | 0.53 | 0.31 | 0 | 0.11 | 5.06 | 0.7 | 0.34 | 0.46 |
| Rk3 | 0 | 0 | 0 | 0.07 | 1.97 | 0.17 | 0.22 | 0.16 |
| Rh4 | 0 | 0 | 0 | 0.12 | 8.96 | 0.78 | 0.69 | 0.69 |
| 20S-Rg3 | 0 | 0 | 0 | 0 | 1.24 | 0.12 | 0.39 | 0.36 |
| 20R-Rg3 | 0 | 0 | 0 | 0 | 0.86 | 0.15 | 0.4 | 0.29 |
| Rk1 | 0 | 0.02 | 0 | 0 | 0.88 | 0.06 | 0.49 | 0.44 |
| Rg5 | 0.04 | 0.01 | 0 | 0.03 | 0.66 | 0.05 | 0.27 | 0.2 |
| Rh2 | 0 | 0 | 0 | 0.02 | 0.05 | 0.01 | 0 | 0 |
| total saponin | 26.15 | 7.27 | 12.59 | 13.69 | 28.63 | 6.55 | 14.44 | 14.63 |
| Rare saponin content | 0.57 | 0.34 | 0 | 0.35 | 19.68 | 2.04 | 2.8 | 2.6 |
| Proportion of rare saponins to total saponins/% | 2.18 | 4.68 | 0.00 | 2.56 | 68.74 | 31.15 | 19.39 | 17.77 |

As can be seen from Table 2, 17 ginsenosides can be detected under this assay condition, and the total saponin (liquid phase method) is the sum of these 17 ginsenosides, among which there are 8 rare ginsenosides, namely F2, RK3, Rh4, 20S-Rg3, 20R-Rg3, Rk1, Rg5 and Rh2.

Under these conditions, there was little difference in the total saponin content of ginseng stems and leaves extracts and ginseng roots extracts before and after the enzymatic hydrolysis and heat treatment, but the percentage of rare ginsenosides was significantly increased. This indicates that common ginsenosides in the extracts were converted into rare ginsenosides after the enzymatic hydrolysis and heat treatment.

Example 2: Preparation of Ginseng Extract Rich in Rare Ginsenosides by Enzymatic Hydrolysis and Heat Treatment 1) Preparation of Ginseng Stems and Leaves Extract Dry Powder and Ginseng Root Extract Dry Powder
   Same as embodiment I.
2) "Enzymatic and Heat Treatment" Preparation Process
   (1) Batch No. XRSY230303: ginseng stems and leaves extract dry powder (homemade, Batch No. RSY230201) was prepared with water to form a 20% concentration of the substrate, adjusted the pH to 5.0, and added with 5 U/g of β-glucosidase, with the enzymatic hydrolysis temperature at 60° C. and the enzymatic hydrolysis time of 5 h, and the heat-treatment temperature at 132° C., the heat-treatment pressure of 200 kPa, and the time of the heat-treatment was 1 h.
   (2) Batch No. XRSG230303: ginseng roots extract dry powder (homemade, Batch No. RSG230201) was prepared with water to form a 20% concentration of the substrate, adjusted the pH to 5.0, and added with 5 U/g of β-glucosidase, with the enzymatic hydrolysis temperature at 60° C. and the enzymatic hydrolysis time of 5 h, and the heat treatment temperature at 132° C., the heat treatment pressure at 200 kPa, and the heat treatment time of 1 h.
   (3) Batch No. XRSY230304: ginseng stems and leaves extract dry powder (Hanzhong Natural Valley Biotechnology Co., Ltd., Batch No. Crs230310) was prepared with water to form a 20% concentration of the substrate, adjusted the pH to 5.0, and added with 5 U/g of β-glucosidase, with the enzymatic hydrolysis temperature at 60° C. and the time of enzymatic hydrolysis of 5 h, and the temperature of heat treatment at 132° C., and the pressure of heat treatment at 200 kPa. The heat treatment time was 1 h.
   (4) Batch No. XRSG230304: Ginseng root extract dry powder (Hongjiu Biotechnology Co., Ltd, Batch No. S220406) was prepared with water to form a 20% concentration of the substrate, adjusted the pH to 5.0, and added with 5 U/g of β-glucosidase, with the enzymatic hydrolysis temperature at 60° C. and the time of enzymatic hydrolysis of 5 h, and the temperature of heat treatment at 132° C., the pressure of heat treatment at 200 kPa, and the time of heat treatment of 1 h.

The extracts obtained from the above (1)-(4) "Enzymatic hydrolysis and heat treatment" were concentrated, the concentration temperature was 85° C., the concentration pressure was −0.05 Mpa, and the concentration was concentrated to the specific gravity of 1.20 (25° C.). The concentrate was spray dried by centrifugal type with the following parameters: inlet air temperature 160° C., outlet air temperature 100° C., centrifugal frequency 280 Hz, induced air frequency 60 Hz, feed pump 40 RPM, i.e. the extract powder rich in rare ginseng saponins was obtained.

(3) Physicochemical Indexes of Spray-Dried Products (Extract Powder Rich in Rare Ginsenosides) were Tested.

Among them, the results of yield, particle size, moisture and ash are shown in Table 3.

TABLE 3

| Physicochemical indexes of spray-dried products-1 | | | | |
| --- | --- | --- | --- | --- |
| Batch number | Yield | Particle size (80 mesh sieve) | Padding | Ash |
| XRSY230303 | 82.56% | 90.02% | 1.95% | 0.30% |
| XRSY230304 | 83.02% | 90.05% | 1.86% | 0.39% |
| XRSG230303 | 80.02% | 85.24% | 2.21% | 0.35% |
| XRSG230304 | 82.27% | 86.15% | 2.25% | 0.35% |

Note:
Yield: weight of dry powder obtained after "enzymatic hydroysis + heat treatment"/weight of dry powder of ginseng extract before treatment * 100%;
Particle size (after 80 mesh sieve): weight of dry powder after 80 mesh sieve/total dry powder before sieve * 100%;
Ash: conducted in accordance with GB 5009.4-2016 National Standard for Food Safety Determination of Ash in Food.

The extract powder enriched with rare ginsenosides was assayed as in Example 1, and the results are shown in Table 4.

TABLE 4

| | Content before treatment (%, g/100 g) | | | | Content after "enzymatic hydrolysis + heat treatment" (%, g/100 g) | | | |
| --- | --- | --- | --- | --- | --- | --- | --- | --- |
| Ginsenoside Standard | RSY230201 | Crs230310 | RSG230201 | S220406 | XRSY230303 | XRSY230304 | XRSG230303 | XRSG230304 |
| Re | 3.53 | 1.27 | 0.84 | 1.34 | 1.22 | 0.69 | 0.77 | 1.12 |
| Rg1 | 10.64 | 3.02 | 2.2 | 2.22 | 2.26 | 1.6 | 1.19 | 1.65 |
| Rf | 0 | 0 | 0.4 | 0.51 | 0 | 0 | 0.4 | 0.4 |
| Rb1 | 2.72 | 0.47 | 3.05 | 2.92 | 0.77 | 0.27 | 2.42 | 1.84 |
| Rc + Rh1 | 1.83 | 0.33 | 2.08 | 2.2 | 1.81 | 0.29 | 1.67 | 1.65 |
| Rb2 | 2.63 | 0.49 | 2.98 | 2.33 | 3.2 | 0.52 | 2.2 | 2.52 |
| F1 | 1.05 | 0.36 | 0 | 0 | 0.85 | 0.22 | 0 | 0 |
| Rd | 3.18 | 0.99 | 1.04 | 1.82 | 2.91 | 0.92 | 1 | 0.86 |
| F2 | 0.53 | 0.31 | 0 | 0.11 | 5.22 | 0.7 | 0.24 | 0.35 |
| Rk3 | 0 | 0 | 0 | 0.07 | 2.08 | 0.17 | 0.18 | 0.32 |
| Rh4 | 0 | 0 | 0 | 0.12 | 9.25 | 0.78 | 0.8 | 0.30 |
| 20S-Rg3 | 0 | 0 | 0 | 0 | 1.11 | 0.12 | 0.29 | 0.32 |
| 20R-Rg3 | 0 | 0 | 0 | 0 | 0.8 | 0.15 | 0.26 | 0.29 |

TABLE 4-continued

| | Physicochemical indexes of spray-dried products-2 | | | | | | | |
| | Content before treatment (%, g/100 g) | | | | Content after "enzymatic hydrolysis + heat treatment" (%, g/100 g) | | | |
| Ginsenoside Standard | RSY230201 | Crs230310 | RSG230201 | S220406 | XRSY230303 | XRSY230304 | XRSG230303 | XRSG230304 |
|---|---|---|---|---|---|---|---|---|
| Rk1 | 0 | 0.02 | 0 | 0 | 0.76 | 0.06 | 0.35 | 0.32 |
| Rg5 | 0.04 | 0.01 | 0 | 0.03 | 0.58 | 0.05 | 0.17 | 0.20 |
| Rh2 | 0 | 0 | 0 | 0.02 | 0.03 | 0.01 | 0 | 0 |
| total saponin | 26.15 | 7.27 | 12.59 | 13.69 | 32.85 | 6.55 | 11.94 | 12.14 |
| Rare saponin content | 0.57 | 0.34 | 0 | 0.35 | 19.83 | 2.04 | 2.29 | 2.1 |
| Proportion of rare saponins to total saponins/% | 2.18 | 4.68 | 0.00 | 2.56 | 60.37 | 31.15 | 19.18 | 17.30 |

As can be seen from Table 4, 17 ginsenosides can be detected under this assay condition, and the total saponin (liquid phase method) is the sum of these 17 ginsenosides, among which there are 8 rare ginsenosides, namely F2, RK3, Rh4, 20S-Rg3, 20R-Rg3, Rk1, Rg5 and Rh2.

Under these conditions, there was little difference in the total saponin content of ginseng stems and leaves extracts and ginseng roots extracts before and after the enzymatic hydrolysis and heat treatment, but the percentage of rare ginsenosides was significantly increased. This indicates that common ginsenosides in the extracts were converted into rare ginsenosides after the enzymatic hydrolysis and heat treatment.

Embodiment 3: Preparation of Ginseng Extract Rich in Rare Ginsenosides by Enzymatic Hydrolysis and Heat Treatment 1) Preparation of Ginseng Stems and Leaves Extract Dry Powder and Ginseng Root Extract Dry Powder
Same as Example 1.
2) "Enzymatic and Heat Treatment" Preparation Process
    (1) Batch No. XRSY230305: ginseng stems and leaves extract dry powder (homemade, Batch No. RSY230201) was prepared with water to form a 10% concentration of the substrate, adjusted pH to 4.3, and added with 2 U/g of β-glucosidase, the enzymatic hydrolysis temperature was 40° C., the time of enzymatic hydrolysis was 3 h, the temperature of heat treatment was 121° C., the pressure of heat treatment was 110 kPa, and the time of heat treatment was 4 h.
    (2) Batch No. XRSG230305: ginseng roots extract dry powder (homemade, batch No. RSG230201) was prepared with water to form a 10% concentration of the substrate, adjusted the pH to 4.3, and added with 2 U/g β-glucosidase, the enzymatic hydrolysis temperature was 40° C., the time of enzymatic hydrolysis was 3 h, the temperature of the heat treatment was 121° C., the pressure of the heat treatment was 110 kPa, and the time of the heat treatment was 4 h.
    (3) Batch No. XRSY230306: ginseng stems and leaves extract dry powder (Hanzhong Natural Valley Biotechnology Co., Ltd., Batch No. Crs230310) was prepared with water to form a 10% concentration of the substrate, adjusted the pH to 4.3, and added with 2 U/g of β-glucosidase, the enzymatic hydrolysis temperature was 40° C., the time of enzymatic hydrolysis was 3 h, the temperature of the heat treatment was 121° C., and the pressure of the heat treatment was 110 kPa. The heat treatment time was 4 h.
    (4) Batch No. XRSG230306: Ginseng root extract dry powder (Hongjiu Biotechnology Co., Ltd, Batch No. S220406) was prepared with water to form a 10% concentration of the substrate, adjusted the pH to 4.3, and added with 2 U/g of β-glucosidase, the enzymatic hydrolysis temperature was 40° C., the time of enzymatic hydrolysis was 3 h, the temperature of the heat treatment was 121° C., the pressure of the heat treatment was 110 kPa, and the time of the heat treatment was 4 h.

The extracts obtained from the above (1)-(4) "Enzymatic hydrolysis and heat treatment" were concentrated respectively, the concentration temperature was 75° C., the concentration pressure was −0.09 Mpa, and the concentration was made to the specific gravity of 1.10 (25° C.). The obtained concentrate was spray dried by centrifugal type with the following parameters: inlet air temperature 135° C., outlet air temperature 80° C., centrifugal frequency 250 Hz, induced air frequency 55 Hz, feed pump 10 RPM, i.e. the extract powder rich in rare ginseng saponins was obtained.
(3) Physicochemical Indexes of Spray-Dried Products (Extract Powder Rich in Rare Ginsenosides) were Tested.

Among them, the results of yield, particle size, moisture and ash are shown in Table 5.

TABLE 5

| | Physical and chemical indexes of spray-dried products-1 | | | |
| Batch number | Yield | Particle size (80 mesh sieve) | Padding | Ash |
|---|---|---|---|---|
| XRSY230305 | 92.25% | 93.85% | 2.68% | 0.36% |
| XRSY230306 | 91.02% | 91.68% | 3.50% | 0.39% |
| XRSG230305 | 90.68% | 94.31% | 3.81% | 0.32% |
| XRSG230306 | 90.00% | 90.00% | 3.25% | 0.38% |

Note:
Yield: weight of dry powder obtained after "enzymatic hydrolysis + heat treatment"/weight of dry powder of ginseng extract before treatment * 100%;
Particle size (after 80 mesh sieve): weight of dry powder after 80 mesh sieve/total dry powder before sieve * 100%;
Ash: conducted in accordance with GB 5009.4-2016 National Standard for Food Safety Determination of Ash in Food.

The extract powder enriched with rare ginsenosides was assayed as in Example 1, and the results are shown in Table 6.

TABLE 6

| Physical and chemical indexes of spray-dried products-2 | | | | | | | |
| Ginsenoside Standard | Content before treatment (%, g/100 g) | | | | Content after "enzymatic hydrolysis + heat treatment" (%, g/100 g) | | | |
| | RSY230201 | Crs230310 | RSG230201 | S220406 | XRSY230305 | XRSY230306 | XRSG230305 | XRSG230306 |
|---|---|---|---|---|---|---|---|---|
| Re | 3.53 | 1.27 | 0.84 | 1.34 | 0.75 | 0.6 | 0.72 | 1.17 |
| Rg1 | 10.64 | 3.02 | 2.2 | 2.22 | 1.56 | 1.66 | 1.61 | 1.60 |
| Rf | 0 | 0 | 0.4 | 0.51 | 0 | 0.03 | 0.44 | 0.55 |
| Rb1 | 2.72 | 0.47 | 3.05 | 2.92 | 0.4 | 0.28 | 1.56 | 1.03 |
| Rc + Rh1 | 1.83 | 0.33 | 2.08 | 2.2 | 1.54 | 0.39 | 1.69 | 1.72 |
| Rb2 | 2.63 | 0.49 | 2.98 | 2.33 | 2.69 | 0.56 | 2.97 | 2.56 |
| F1 | 1.05 | 0.36 | 0 | 0 | 0.58 | 0.25 | 0 | 0.1 |
| Rd | 3.18 | 0.99 | 1.04 | 1.82 | 2.92 | 1.17 | 0.98 | 0.78 |
| F2 | 0.53 | 0.31 | 0 | 0.11 | 5.31 | 0.89 | 0.24 | 0.34 |
| Rk3 | 0 | 0 | 0 | 0.07 | 1.9 | 0.22 | 0.12 | 0.19 |
| Rh4 | 0 | 0 | 0 | 0.12 | 8.71 | 1.11 | 0.68 | 0.80 |
| 20S-Rg3 | 0 | 0 | 0 | 0 | 1.15 | 0.16 | 0.24 | 0.15 |
| 20R-Rg3 | 0 | 0 | 0 | 0 | 0.77 | 0.1 | 0.21 | 0.19 |
| Rk1 | 0 | 0.02 | 0 | 0 | 0.69 | 0 | 0.49 | 0.14 |
| Rg5 | 0.04 | 0.01 | 0 | 0.03 | 0.54 | 0.07 | 0.27 | 0.18 |
| Rh2 | 0 | 0 | 0 | 0.02 | 0.03 | 0 | 0 | 0 |
| total saponin | 26.15 | 7.27 | 12.59 | 13.69 | 29.54 | 7.49 | 12.22 | 11.5 |
| Rare saponin content | 0.57 | 0.34 | 0 | 0.35 | 19.1 | 2.55 | 2.25 | 1.99 |
| Proportion of rare saponins | | | 0.00 | | | | 18.41 | |
| to total saponins/% | 2.18 | 4.68 | | 2.56 | 64.66 | 34.05 | | 17.30 |

As can be seen from Table 6, 17 ginsenosides can be detected under this assay condition, and the total saponin (liquid phase method) is the sum of these 17 ginsenosides, among which there are 8 rare ginsenosides, namely F2, RK3, Rh4, 20S-Rg3, 20R-Rg3, Rk1, Rg5 and Rh2.

Under these conditions, there was little difference in the total saponin content of ginseng stems and leaves extracts and ginseng roots extracts before and after the enzymatic hydrolysis and heat treatment, but the percentage of rare ginsenosides was significantly increased. This indicates that the common ginseng sides in the extracts were converted into rare ginsenosides after the enzymatic hydrolysis and heat treatment.

Embodiment 4—In Vitro Antioxidant Test

Measurement of Antioxidant Capacity

Samples (8 parts of dried ginseng extract powder from embodiment 1) were prepared:

Weigh 1 g of sample in 10 mL volumetric flask, add methanol, sonicate for 30 minutes, cool to room temperature, dilute with methanol, shake well and filter through 0.22 μm membrane. Dilute with methanol to 1, 2, 3, 4, 5, 6, 8, 10 mg/ml respectively.

1) Measurement of DPPH Free Radical Scavenging Capacity

Take 4 g DPPH with anhydrous ethanol to 100 mL volumetric flask, prepare DPPH solution with concentration of 0.04 mg/mL and leave it in the light; respectively, take 0.1 mL ginseng extract samples (concentration of 2, 4, 6, 8, and 10 mg/ml) and add it into the newly prepared 3.9 mL DPPH solution, mix well, and react for 60 min at 37° C. under the condition of water bath, and the absorbance was measured at 517 nm. The absorbance was measured at 517 nm and the formula was calculated as follows:

$$\text{DPPH free radical scavenging rate}/\% = [1 - (A1 - A2)/A3] \times 100\%$$

In the formula: A1 is the absorbance of 3.9 mL DPPH+0.1 mL of sample; A2 is the absorbance of 3.9 mL ethanol+0.1 mL of sample; and A3 is the absorbance of 3.9 mL DPPH+0.1 mL ethanol.

Figure 2:
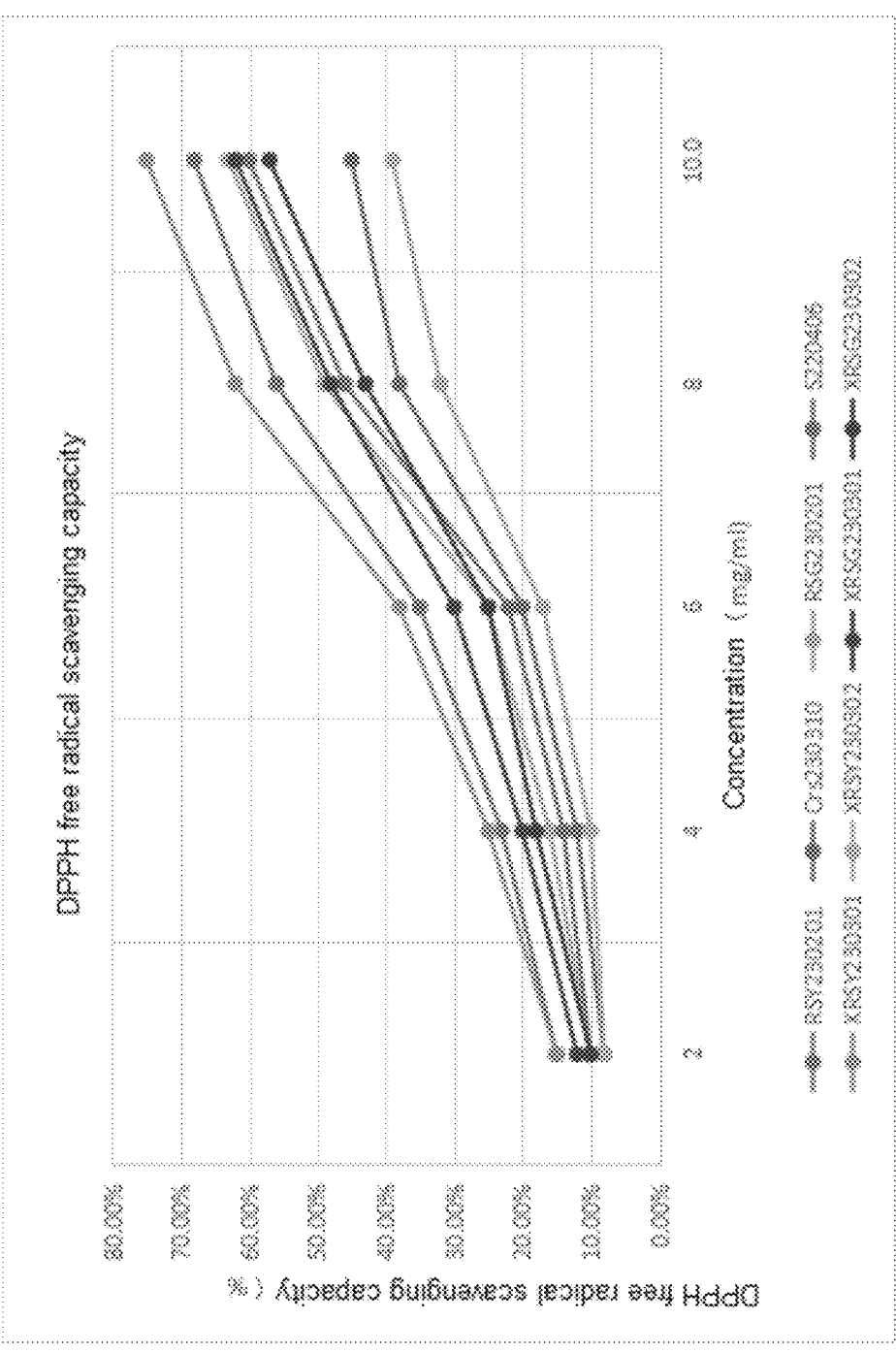
FIG. 2 shows the variation of DPPH free radical scavenging capacity of different ginseng extracts of the present invention.

The changes in DPPH radical scavenging ability of different ginseng extracts are shown in FIG. 2.

The DPPH radical is a very stable nitrogen-centered radical that can express inhibitory effects on hydroxyl, alkyl and peroxyl radicals. As shown in FIG. 2, the scavenging ability of different ginseng extracts on DPPH radicals showed a dose-dependent effect, with ginseng stems and leaves extract (batch XRSY230301), which is rich in rare ginsenosides, having the strongest scavenging ability on DPPH radicals.

2) ABTS$^+$ Determination of Free Radical Scavenging Capacity

Take the same volume of 7.4 mmol/L ABTS solution and 2.6 mmol/L K S O$_{228}$ solution, placed in a 100 mL brown wide-mouth bottle, mixed well, at room temperature (20° C.) static for 12 h~16 h, and then diluted 45 times with anhydrous ethanol as the ABTS working solution (OD734 nm=0.7±0.02) for spare. Take 0.2 mL of the sample (concentration of 1, 2, 3, 4, 5 mg/mL, respectively), add to 0.8 mL ABTS working solution, shaking 10 s, mix thoroughly, and then leave it to stand for 6 min away from light, and measure the absorbance at 734 nm as A1, and substitute 0.2 mL of ethanol for the sample as a blank group, and measure the absorbance A0, the calculation formula is as follows:

$$\text{ABTS}^+ \text{ Free radical scavenging rate}/\% = (1 - A1/A0) \times 100\%$$

Figure 3:
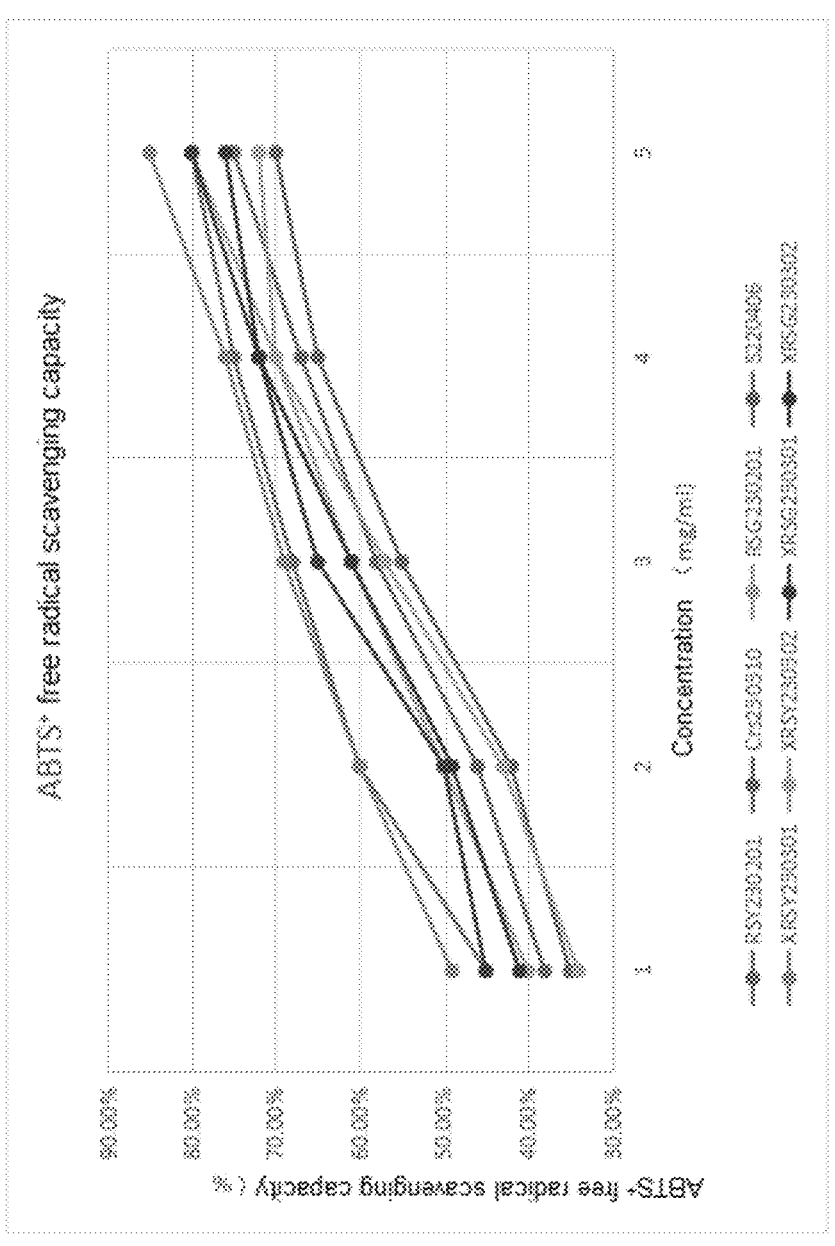
FIG. 3 shows the variation of free radical scavenging capacity of different ginseng extracts ABTS⁺ of the present invention.

Changes in free radical scavenging capacity of ABTS⁺ by different ginseng extracts are shown in FIG. 3.

The ABTS⁺ free radical scavenging assay is an important method to determine the antioxidant capacity of compounds. As shown in FIG. 3, the scavenging ability of different ginseng extracts on ABTS⁺ free radicals showed a dose-dependence, and the ginseng stems and leaves extract (batch XRSY230301), which is enriched with rare ginsenosides, had the strongest scavenging ability on ABTS⁺ free radicals.

3) Measurement of Hydroxyl Radical Scavenging Capacity

Take 2 mL of the sample (concentration of 1, 2, 3, 4, 5 mg/mL, respectively), add 1 mL of 0.75 mmol/L o-diazophene solution, 2 mL of 0.2 mol/L phosphate buffered saline (PBS) (pH 7.4), mix well and then add 1 mL of 0.75 mmol/L ferrous sulfate solution, 1 mL of 0.01% hydrogen peroxide solution, mix well and then measure the absorbance at 536 nm in a water bath at 37° C. for 1 h. The control group used distilled water instead of hydrogen peroxide solution, and the blank group measured the absorbance at 536 nm. and 1 mL 0.01% hydrogen peroxide solution, mixed well and then in a water bath at 37° C. for 1 h. The absorbance was measured at 536 nm. Distilled water was used to replace the hydrogen peroxide solution in the control group, and distilled water was used to replace the sample in the blank group, and the formula was calculated as follows:

$$\text{Hydroxyl radical scavenging rate/\%} = (As - Ac)/(Ab - Ac)$$

In the formula: As is the absorbance of the test sample; Ac is the absorbance of the control group; Ab is the absorbance of the blank group.

Figure 4:
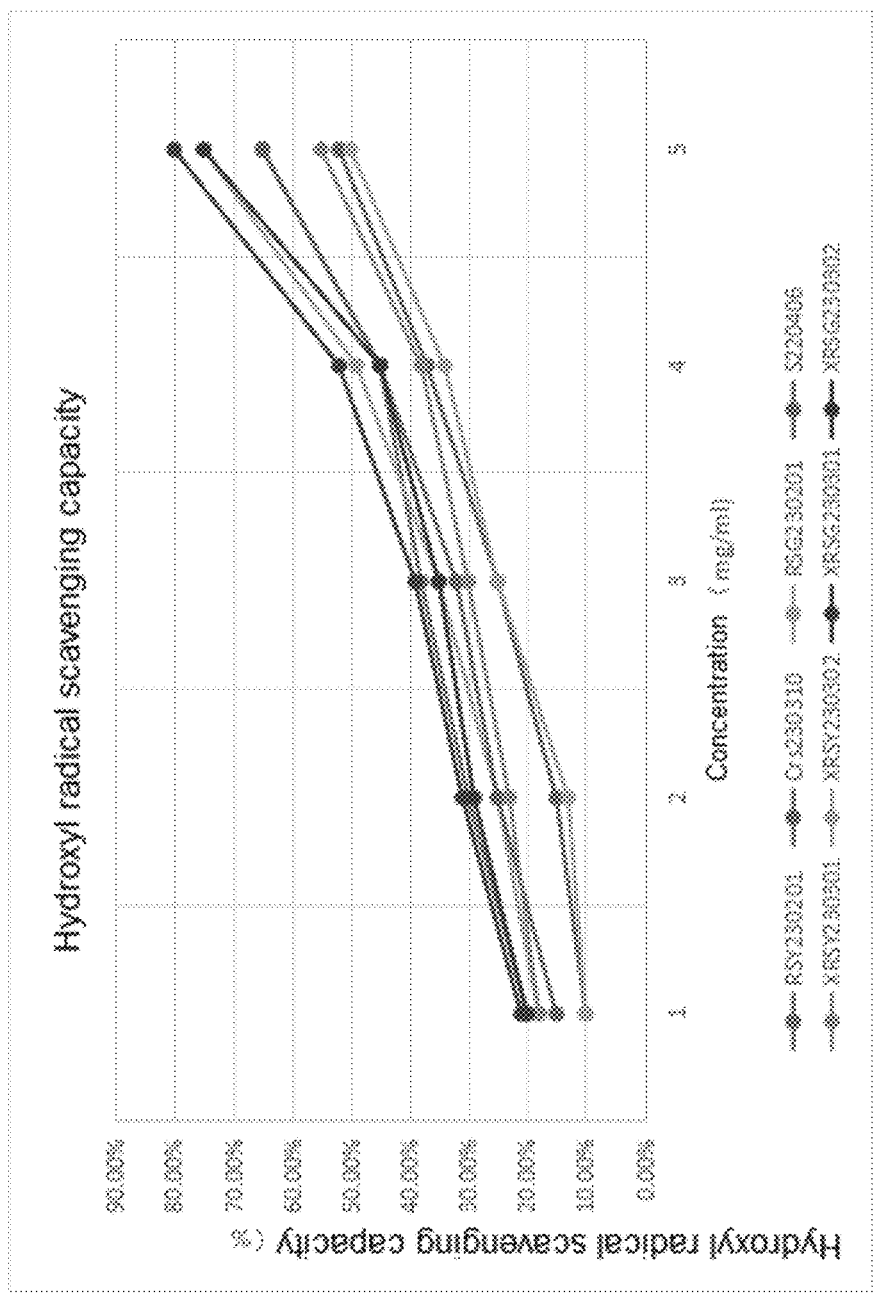
FIG. 4 shows the variation of hydroxyl radical scavenging capacity of different ginseng extracts of the present invention.

Hydroxyl radicals are the most active oxygen radicals among reactive oxygen species and the most toxic ones, which are the main factors causing damage to organisms. The variation of hydroxyl radical scavenging ability of different ginseng extracts is shown in FIG. 4. From FIG. 4, it can be seen that the scavenging ability of different ginseng extracts on hydroxyl radicals showed dose-dependence, and ginseng roots extracts rich in rare ginsenosides (batch XRSG230301) had the strongest scavenging ability on hydroxyl radicals. Combined with the content index of ginsenosides (liquid phase method) and the literature, it suggests that the scavenging ability of hydroxyl radicals, except ginsenosides, correlates with polysaccharides and glycosides in ginseng extracts.

4) Measurement of Superoxide Anion Radical Scavenging Capacity

Take 2 mL of sample (concentration of 1, 2, 3, 4, 5 mg/mL, respectively), 4 mL of 0.05 mol/L Tris-HCl solution (pH 8.2), and heat at 25° C. for 20 min; remove and add 60 μL of 25 mmol/L o-toluene trisol solution, mix thoroughly at 25° C. and heat for 5 min; remove and add 200 μL of 10 mmol/L hydrochloric acid solution to terminate the reaction; measure the absorbance at 325 nm. L hydrochloric acid solution, the reaction was terminated and the absorbance was measured at 325 nm.

$$\text{Superoxide anion radical scavenging rate/\%} = [1 - (A1 - A2)/A3] \times 100\%$$

Where: A1 is the absorbance of 60 μL of catechol+2 mL of sample; A2 is the absorbance of 60 μL of distilled water+2 mL of sample; A3 is the absorbance of 60 μL of catechol+2 mL of distilled water.

Figure 5:
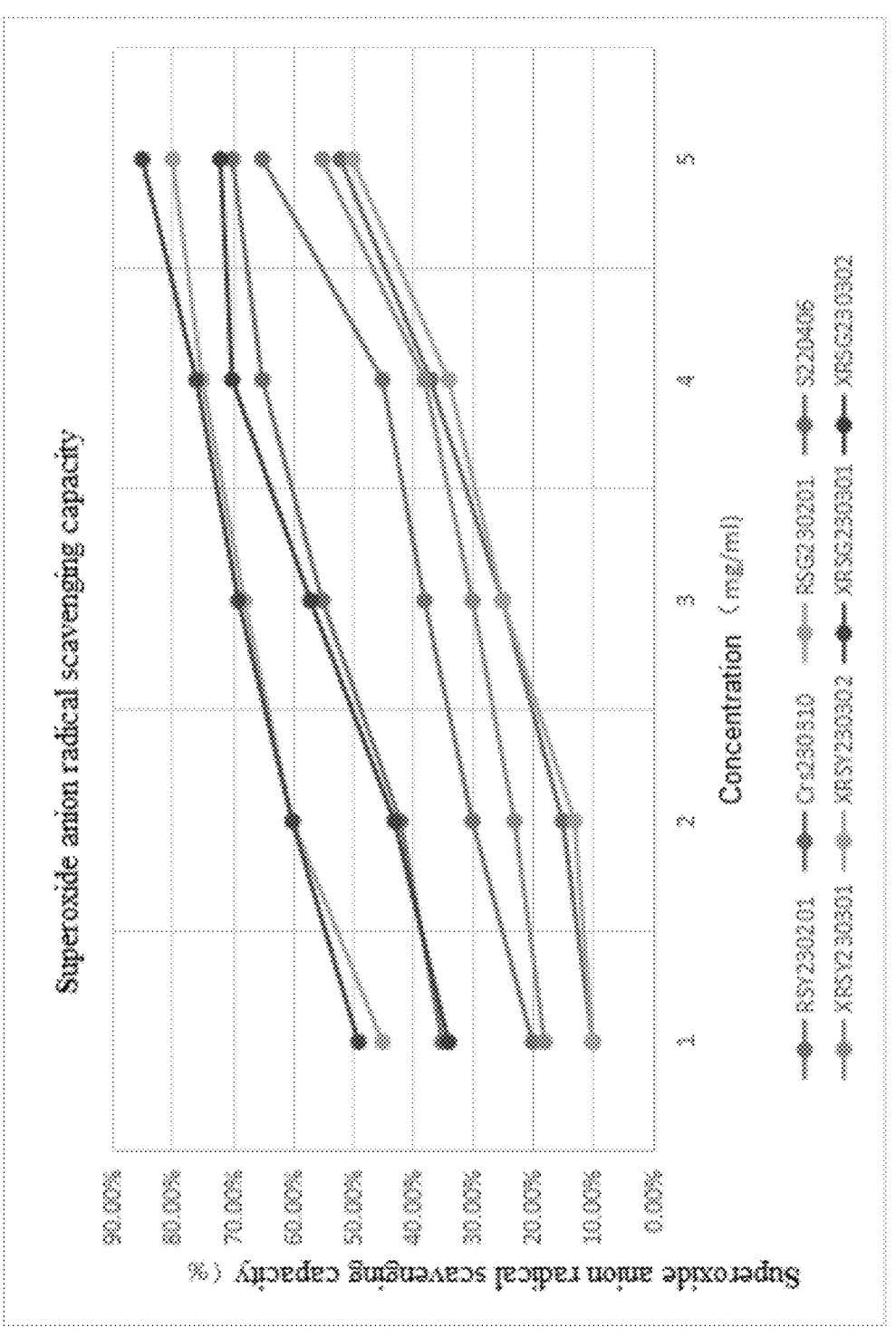
FIG. 5 shows the variation of superoxide anion radical scavenging capacity of different ginseng extracts of the present invention.

Superoxide anion radicals are the longest-lived free radicals in the organism and are usually used as initiators of free radical chain reactions to produce more active free radicals. The changes in the scavenging ability of different ginseng extracts for superoxide anion radicals are shown in FIG. 5. As can be seen from the FIG. 5, the scavenging ability of different ginseng extracts for superoxide anion radicals showed a dose-dependence, and the scavenging ability of the ginseng roots extract (batch XRSG230301), which is enriched with rare ginsenosides, was the strongest, and the ginseng roots-related extracts were better than the ginseng stem and leaf-related extracts for the scavenging ability of superoxide anion radicals. The ginseng roots related extracts had better scavenging ability than the ginseng stem and leaf related extracts for superoxide anion radicals. Combined with the content index of ginsenosides (liquid phase method) and the literature, the scavenging ability of ginseng extracts for superoxide anion radicals was correlated with the polysaccharides and glycosides in ginseng extracts, except for ginsenosides.

As mentioned above, combined with the literature, ginseng roots extract rich in rare ginsenosides (batch XRSG230301) had the strongest scavenging ability for hydroxyl radicals and superoxide anion radicals, and slightly weaker scavenging ability for DPPH and ABTS±radicals. Taken together, the in vitro antioxidant capacity of ginseng roots extracts enriched with rare ginsenosides was superior.

Embodiment 5: Anti-Deterioration Experiment of *Cryptosporidium hirsutum* Nematode Aging not only accelerates the decline of body functions, but also leads to an increase in the incidence of many degenerative diseases, such as Alzheimer's disease, Parkinson's disease, cardiovascular diseases and tumors, etc. In order to reveal the mechanism of aging, the corresponding aging model is usually set up to conduct research, in which the use of cryptic nematode Hididradenosaurs to study the process of aging has the advantages of a short experimental period, easy to detect, and rich and clear genetic background. Among them, the advantages of short experimental period and easy to detect and rich and clear genetic background for the study of aging process using *Cryptosporidium hirsutum* have made *Cryptosporidium hirsutum* a major model organism of aging.

In this experiment, the effects of the product of interest and its components on viability (lifespan and healthy lifespan), antioxidant capacity, and mitochondrial health were tested through a series of standardized analytical methods using the *Cryptobacterium hidradii* nematode (from InVivo Biosystems) as an animal model.

1) Test Article:

Ginseng roots extract rich in rare ginsenosides, Lot XRSG230301, prepared in embodiment I. Yield: 90.10%, converted to herb yield of 32.57%.

Poria Extract: Poria blocks crushed through a sieve 80 mesh, add 6-8 times the drinking water boiled for 3 hours, concentrated and spray-dried. Yield: 82.42%.

Radix rehmanniae extract: 50% ethanol reflux extraction 3 times, adding liquid amount of 6, 6, 5 times the amount of each extraction for 2 hours, concentrated and spray-dried. Yield 43.24%.

JadeAging: The above ginseng extracts rich in rare ginsenosides, the poria extract, the radix rehmanniae are compounded according to 15%, 46% and 39%.

2) Test Process (1) The experimental groupings are shown in Table 7.

TABLE 7

| Groups | Drug(s) |
| --- | --- |
| blank group | VC (vehicle control, no drug treatment controlling group) |
| Sample 1 | JadeAging (Ginseng + Poria + Rehmannia) |
| Sample 2 | Ginseng (XRSG, ginseng root extract rich in rare ginsenosides) |
| Sample 3 | Poria (*Poria cocos* extract) |
| Sample 4 | Rehmannia (*radix rehmanniae*) |

(2) Preparation of Reserve Solution

The above samples were dissolved in 10% DMSO, dispersed by ultrasonication, and then sterilized through a 0.2 µm filter to make a stock solution of 100 mg/mL. For use, the stock solution was diluted with 0.1% DMSO to the concentration required for each test.

(3) Concentration Screening

High-resolution imaging and automated assays are used to accurately measure growth rates of animals from hatching to the first day of adulthood. Growth and developmental assays for *Cryptobranchus hidradii* nematodes are highly sensitive to chemical or nutritional perturbations and are widely used in toxicology studies. Conducting this test over a range of doses helps to identify a set of doses that have physiological effects and to exclude a range of doses that may be toxic but beneficial to the animal during its lifespan.

Based on the papers, seven concentrations were selected to be tested for production and developmental outcomes to determine their effects on growth and compared to a blank group (VC group).

Figure 6:
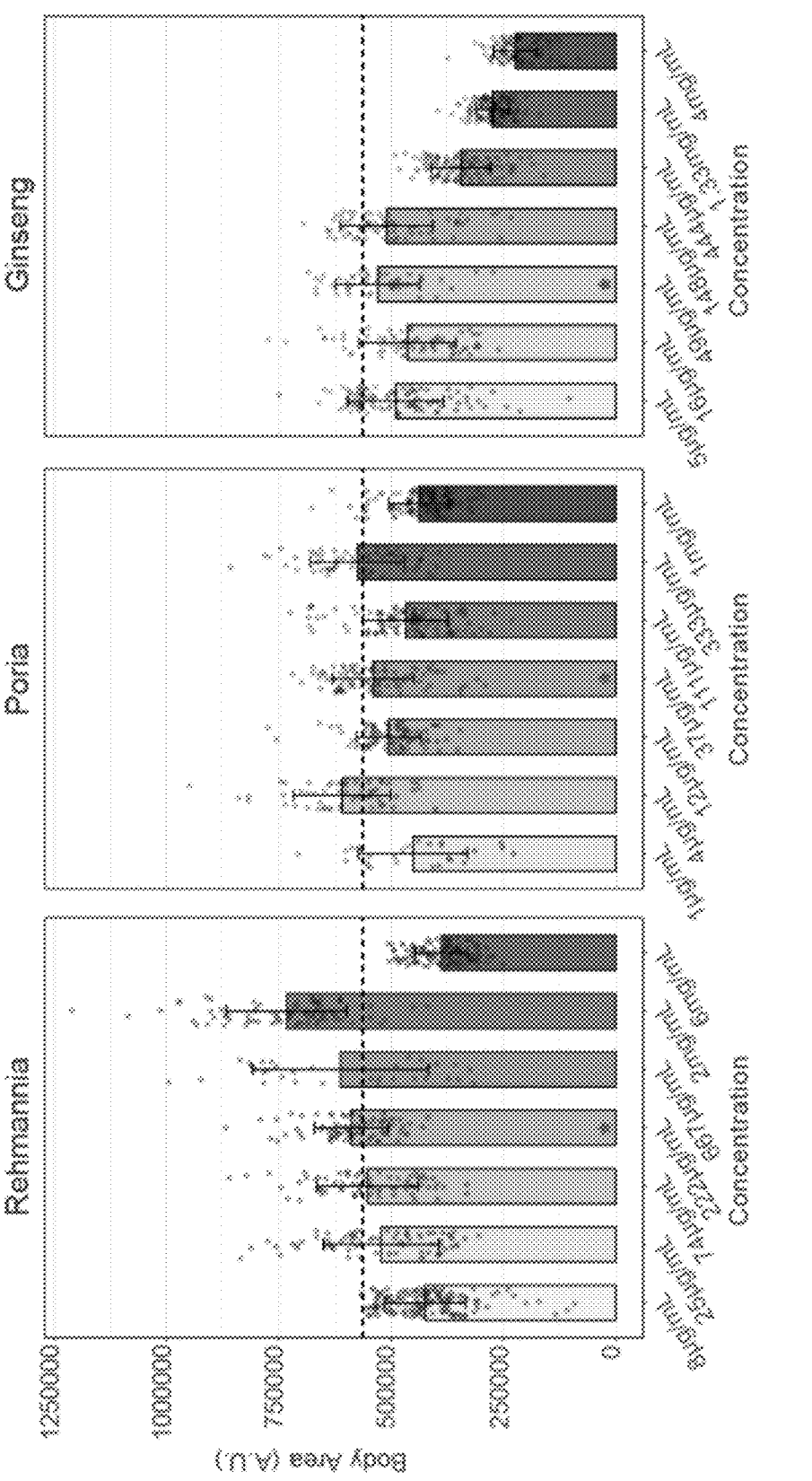
FIG. 6 shows the size of the showy cryptic rod nematode of the present invention as an adult.

The average size of adult (4 days post-hatch) nematodes was obtained by high-resolution imaging and automated detection and tracking software (WormLab), and the results are shown in FIG. 6. The dashed line identifies the average size of nematodes in the blank group, and the size was quantified as area.

Compared to the blank group (VC group) (dotted line), Rehmannia (geomannia extract) promoted nematode growth; however, differences in nematode size increased significantly at the higher doses tested, suggesting that the optimal dose for the effect of Rehmannia (geomannia extract) on nematode longevity would be less than 667 µg/mL. Poria (*Poria cocos* extract) did not cause a concentration-dependent size changes. Ginseng (ginseng extract rich in rare ginsenosides) showed growth inhibition at concentrations above 148 µg/mL indicating that lower concentrations are optimal for testing the effects of Ginseng on nematodes.

CONCLUSION: Based on the growth and developmental assays, the concentration of each compound was selected which gave the best growth in the growth and developmental assays. Rehmannia (Groundnut Extract) was set at 220 µg/mL, Poria (Poria Extract) was set at 37 µg/mL, Ginseng (Ginseng Extract enriched with rare ginseng saponins) was set at 50 µg/mL, while JadeAging was set at 100 µg/mL.

(4) Vitality Experiment

To determine whether JadeAging, Ginseng, Poria, and Rehmannia affect health and longevity, selected concentrations of each compound were measured in nematodes and the longevity of the populations and activity levels throughout the life course were assessed.

OBJECTIVE: To compare the effects of four treatment groups (Ginseng, Poria, Rehmannia, and JadeAging) and a blank group (VC) on the longevity and health of *Cryptococcus hidradiensis*, and to monitor the survival and motility status of adult *Cryptococcus hidradiensis*.

METHODS: The longevity assay was adapted from the standard protocol used and published by the *Cryptobacterium neoformans* Intervention Trial Program (CITP).

Lifespan results: nematodes were treated with selected concentrations of each compound and compared to a blank group (VC). Lifespan data were expressed as the proportion of nematodes surviving over time, called Kaplan-Meier survival function estimates, and the results are shown in FIG. 7. Overall, no positive effect of the samples to be tested on the increase in lifespan was detected relative to the blank group (VC).

Health span: Movement of *Cryptococcus showyi* nematodes can be quantified throughout the life span. Exercise can indicate energy levels and health status, with older *Cryptobranchus hidradii* nematodes typically exhibiting reduced activity. The percentage of lifespan in each treatment group in these locomotor states is shown in FIG. 8. The results show that the treatment groups all increased the percentage of *hidradenitis elegans* nematodes that exhibited vigorous locomotion throughout their lives, but the improvement was not significant, and the *hidradenitis elegans* nematodes treated with 220 µg/mL Rehmannia (extract of the groundnut) exhibited vigorous locomotion throughout a greater percentage of their lives.

As mentioned above, JadeAging, Ginseng, Poria, and Rehmannia did not significantly improve the healthy lifespan of *Cryptococcus showyi* nematodes under the conditions and concentrations tested.

(5) Antioxidant Test

Reactive oxygen species (ROS) are molecules produced by normal cellular metabolism and exposure to environmental factors such as pollutants and radiation. Excessive amounts of ROS can damage the body's DNA, RNA, and proteins, leading to severe stress responses and cell death, and antioxidants can mitigate ROS damage. Paraquat is an organic compound commonly used as a herbicide that is known to cause the release of ROS. Tested whether JadeAging, Ginseng, Poria, and Rehmannia could mitigate oxidative damage caused by exposure to the insecticide paraquat.

OBJECTIVE: To determine the antioxidant capacity of the treatment group (JadeAging, Ginseng, Poria, Rehmannia).

METHODS: Population motility was recorded after exposure to 10 mM paraquat (PQT) and treatment of *Hidradenitis elegans* nematodes with the samples to be tested (2 mg/mL Rehmannia, 100 µg/mL Poria, 500 µg/mL Ginseng, 1 mg/mL JadeAging). The population locomotor activity was observed for 24 hours after 10 mM paraquat exposure; the average level of locomotor activity of *Hidradenitis elegans* cryptic rod nematode population after 24 hours of ROS stress.

*Hidradenitis elegans* nematodes were pre-incubated overnight in a blank group (Control, no PQT) or one of the samples to be tested, and the baseline activity of each group of *Hidradenitis elegans* nematodes was recorded for 2 h prior to exposure to 10 mM PQT (dashed line), as shown in FIG. 9.

The motility of the treatment group was compared with that of *Cryptococcus hidradii* nematodes that had not been exposed to PQT or only to PQT after 24 h of exposure to PQT, and the results showed that *Cryptococcus hidradii* nematodes treated with the four samples to be tested were significantly protected against the effects of PQT, as shown in FIGS. 9-10. Prior to PQT treatment, *hidradenitis elegans* nematodes preincubated in any of the samples to be tested exhibited the same activity level as *hidradenitis elegans* nematodes that had never been exposed to PQT; after 24 h of PQT exposure, the activity level of *hidradenitis elegans* nematodes preincubated in the samples to be tested was significantly higher than that of *hidradenitis elegans* nematodes exposed only to PQT, and it was similar to the activity level of *hidradenitis elegans* nematodes that had not been exposed to PQT Similar.

CONCLUSION: JadeAging, Ginseng, Poria, and Rehmannia-treated *Cryptobacterium hidradenii* nematodes had greater activity under oxidative stress than the PQT group, i.e., JadeAging, Ginseng, Poria, and Rehmannia were all protective against oxidative stress, and the protective effect of the compounded JadeAging and the protective effect of compounded JadeAging was stronger.

(6) Mitochondrial Health Test

Skeletal sarcopenia is an age-related loss of muscle and strength. Muscle mitochondrial dysfunction is observed at the onset of skeletal sarcopenia, followed by alterations in skeletal muscle segmental architecture, ultimately leading to decreased movement. In recent years, clinical studies have shown that urolithin A improves mitochondrial health and alleviates muscle decline due to aging. In the present study, the fluorescently labeled myocyte nuclei and mitochondria of *Cryptomeria hidradii* were used to assess whether Jade-Aging could ameliorate age-related dysfunction.

OBJECTIVE: To assess the ability of aging to protect against muscle decline and delay the onset of sarcopenia.

METHODS: SD1347 *C. hidradenitis elegans* nematodes were treated with JadeAging and fluorescently labeled with muscle nuclei and mitochondria, and muscle and mitochondrial health were assessed using confocal microscopy on days 2, 9, and 12 of the adult stage of *C. hidradenitis elegans*. JadeAging-treated *Cryptococcus hidradii* nematodes were compared with blank (VC group) and positive control (urolithin A, Urolithin A)-treated *Cryptococcus hidradii* nematodes.

Fluorescently labeled SD1347 *C. hidradenii* nematodes (from InVivo Biosystems) were placed in petri dishes containing 100 µg/mL JadeAging, 11.4 µg/mL urolithiin A, and a blank group (VC group). On days 2, 9 and 12 of the adult stage of *Hidradenitis elegans* cryptic rod nematode, images of its muscles were taken with a rotating disk confocal microscope as shown in FIG. 11.

Maximum intensity projected confocal images of adult *Cryptobranchus hippocastanum* animals on days 2, 9 and 12 are shown in FIG. 11, all images are from the "head" region. Healthy muscles, i.e., those of the blank group (VC group), are marked by arrows in the day 2 images and are uniformly streaked; those of the blank group (VC group) are marked by arrows in the day 12 images and show uneven fluorescence.

All images were assessed blindly by six viewers who scored each image: 0=fully intact, 1=mildly fragmented, 2=moderately fragmented, and 3=severely fragmented. The distribution of scores for each group of images was compared (FIG. 12) as well as the mean score for each group of animals (FIG. 13).

As expected, the distribution of scores shifted to the right as the nematodes aged (FIG. 12). However, the change in the scores of *Cryptomeria hidradii* nematodes treated with JadeAging and urolithin A was not as significant as that of the nematodes in the blank group (VC group), i.e., the mitochondrial health of the JadeAging and urolithin A groups was superior to that of the blank group (VC group).

FIG. 13 shows that JadeAging and urolithin A had a significant protective effect against the associated skeletal muscle reduction. On day 2 of adult *Hidradenitis elegans* nematode adulthood, the majority of *Hidradenitis elegans* nematode muscle images in all test groups had scores of 0 or 1, indicating that both mitochondria and muscle were healthy. By day 9, the fragmentation scores of the muscle images of *Hidradenium crypticum* nematodes treated with JadeAging were significantly lower than those of the blank group (VC group) (FIG. 12). On day 12, the nematodes were heavily aged and showed severe fragmentation. However, the JadeAging-treated *Cryptococcus hidradii* nematode muscle images exhibited significantly less fragmentation compared to the muscle images of the blank group (VC group), which was comparable to that of the urolithin A-treated *Cryptococcus hidradii* nematode muscle images (FIG. 11).

The above results suggest that JadeAging prevents the loss of muscle and strength associated with aging.

As mentioned above, JadeAging, Ginseng, Poria, and Rehmannia did not show significant positive effects against *Cryptococcus hidradii* nematodes in the vigor test, but all showed excellent antioxidant properties, which protected the nematodes from the deleterious effects of paraquat. In addition, JadeAging protected against age-related muscle decline (skeletal sarcopenia) to a degree comparable to clinically validated urolithin A (Liu et al. 2022). Taken together, these findings support the positive effects of JadeAging, Ginseng, Poria, and Rehmannia in terms of antioxidant resistance to decline.

Embodiment 6—Studies on the Anti-Degradation Mechanism of *Cryptosporidium hirsutum* Nematodes In order to determine the potential mechanisms by which JadeAging exerts its anti-aging effects, mRNA sequencing (RNA-Seq) and metabolomics studies were performed to reveal the overall gene expression and metabolite changes induced by JadeAging feeding to *Cryptobacterium hidradii* nematodes. In this experiment, we collected juvenile (day 2) and adult (day 9) *Cryptobranchus hidradii* nematodes after treating them with Rehmannia (geomannia extract) 220 µg/mL, Poria (Poria extract) 37 µg/mL, Ginseng (ginseng extract enriched with rare ginseng saponins) 50 µg/mL, and JadeAging 100 µg/mL, respectively. *Hidradenitis elegans* nematodes, and gene expression data were analyzed by mapping them to known viability-related pathways to determine the relevant pathways activated or inhibited by treated senescence.

1) Gene Expression Pathway Research

Use mRNA sequencing (RNA-seq) to examine gene expression and determine which biological pathways are affected by exposure to JadeAging, Ginseng, Poria, and Rehmannia to explain the beneficial health effects of Jade-Aging, including mitochondrial health and protection against reactive oxygen species (ROS).

OBJECTIVE: To determine the genetic and cellular pathways of *Cryptobacterium hidradii* nematodes exposed to the effects of JadeAging, Ginseng, Poria, and Rehmannia.

Methods: RNA-seq was used to identify differentially expressed RNA transcripts after exposure to senescence.

The results showed that JadeAging treatment significantly affected the expression of several genes with defined roles in the antifade pathway, including genes involved in stress resistance and autophagy. In pathway analyses, differentially expressed genes were identified using a cutoff value of P<0.1 and a fold change of ±1.25. Of the 93 genes known to be associated with antifade, six were found to be differentially expressed in juvenile (day 2) *Hidradenitis elegans* nematodes exposed to JadeAging, and five were differentially expressed in adult (day 9) *Hidradenitis elegans* nematodes exposed to JadeAging, as shown in Table 8.

synergistic lifespan extension in animals with decreased function in both DAF-2 and RSKS-1 (Chen et al. 2013).

(3) Another major mechanism leading to increased lifespan is through the promotion of autophagy. The nematode homolog CPR-1, encoding histone B, was signifi-

TABLE 8

Differences in aging-related genes between the JadeAging group and the blank group (VC group)

| Genetics | Human Homologous Gene | Protein Expression | Day 2 | | Day 9 | | |
|---|---|---|---|---|---|---|---|
| | | | Variation factor | P-value | Variation factor | P-value | |
| C46G7.1 | RANAEK/PHI-62 | Non-Iconic Proteins | −1.37 | 0.06 | | | |
| GST-4 | gsta1, gsta, gsta3, gsta4, hpgd5 | Glutathione S-transferase 4 | −1.63 | 6.24E−04 | −1.72 | 2.35E−05 | stress response |
| GST-5 | gsta1, gsta, gsta3, gsta4, hpgd5 | Glutathione S-transferase 5 | 3.04 | <1E−10 | 1.43 | 0.01 | |
| GST-10 | gsta1, gsta, gsta3, gsta4, hpgd5 | Glutathione S-transferase | 1.29 | 0.1 | | | |
| SIP-1 | CRYAA, CRYAB, HSPB1, HSPB2, HSPB3, HSPB6, HSPB8 | Stress-inducible protein 1 | | | 1.3 | 0.02 | |
| RSKS-1 | akt1, akt2, akt3, rps6kb1, rps6kb2, sgk1, sgk2, sgk3 | Ribosomal protein S6β kinase | | | −1.34 | 0.09 | Auto phagy/ TOR |
| CRP-1 | CTSB | Tissue Protease B | 1.51 | 9.02E−03 | | | |
| DAF-2 | IGFIR, INSR, INSRR | Insulin-like receptor beta subunit | | | −1.48 | 0.01 | Insulin signaling |
| DAF-12 | nr1h2, nr1h3, nr1h4, nr1i2, rarb, rarg, thrb | Nuclear Hormone Receptor Family Members | 1.35 | 0.08 | | | (sth. or sb) else |

As can be seen in Table 8, key genes of the typical resistance pathway were differentially expressed in JadeAging-treated *Cryptomeria hidradii* nematodes, as follows:

(1) The insulin/insulin-like growth factor-1 signaling pathway (IIS) is a pathway involved in the genetic regulation of lifespan and aging. Loss of function of the insulin receptor DAF-2 may more than double the lifespan of nematodes, a landmark discovery that contributes to the field of aging (Kenyon et al. 1993). DAF-2 expression was down-regulated in JadeAging-treated *Cryptomeria hidradii* nematodes (day 9) (Table 8).

(2) The target of rapamycin (TOR) pathway is an important pathway involved in regulating lifespan by sensing nutrient levels. tOR is a key nutrient-mediated sensor and master regulator of animal growth and energy metabolism (Blackwell et al. 2019). Signaling through TOR involves two distinct protein complexes, mTORC1 and mTORC2, which regulate different physiological processes. mTORC1 acts primarily through the ribosomal protein S6 kinase (S6K), which inhibits the S6K protein encoded by RSKS-1 and significantly extends lifespan (Hansen et al., 2007) (Hansen et al., 2007). There was a slight decrease in RSKS-1 on day 9 in the test group of *Hidradenitis elegans* cryptic rod nematodes (Table 8). Interestingly, the IIS and TOR pathways also interact, showing cantly up-regulated on day 2 in JadeAging-treated *Cryptobacterium hidradii* nematodes (Table 8), and the CPR-1 gene organizes proteolytic control of protein degradation within the lysosome, which is essential for autophagy.

Genes in pathways promoting longevity associated with stress are also differentially expressed, as shown below:

(1) Moderate levels of stress trigger protective responses that promote longevity (Kishimoto, Uno, and Nishida 2018). The transcription factor SKN-1, a homolog of human nuclear respiratory factor (Nrf), acts in concert with DAF-16 to activate transcriptional responses to xenobiotic and oxidative stress (Tullet et al. 2008). DAF-16/SKN-1 is a key effector of insulin signaling, but also interacts with other longevity genes to promote it. Although the expression of SKN-1 and DAF-16 was unchanged, the downstream stress response effectors glutathione transferases (GSTs) were affected. GST-4 was downregulated in *Hidradenitis elegans* nematodes on both day 2 and day 9 after JadeAging treatment (Table 8). In contrast, GST-5 expression was upregulated in day 2 and day 9 *Hidradenitis elegans* nematodes (Table 8), whereas GST-20 expression was moderately upregulated in day 2 adults (Table 8).

(2) Another target of DAF-16 is the stress response protein SIP-1. reduced expression of SIP-1 has been shown to result in reduced lifespan (Morley and Morimoto, 2004). In animals lacking the RSKS-1 gene, SIP-1 expression is slightly elevated (Seo et al. 2013). SIP-1 expression was up-regulated in *Hidradenitis elegans* cryptic rod nematodes treated with JadeAging on day 9 (Table 8).

(3) RNAsek (PHI-62) affects DAF-16-dependent transcription, and knockdown of it decreases lifespan (McCormick et al. 2012). expression of PHI-62 was down-regulated in *Hidradenitis elegans* cryptic nematodes treated with JadeAging on day 2, but was unaffected on day 9 (Table 8).

(4) Lifespan extension is dependent not only on DAF-16, but also on the nuclear hormone receptor DAF-12 (Hsin and Kenyon 1999), Increased levels of DAF-12 result in increased lifespan (Gerisch et al. 2007). DAF12 expression was up-regulated in JadeAging-treated *Hidradenitis elegans* nematodes at day 2 (Table 8).

We also investigated the differentially expressed genes associated with longevity in *Cryptomeria hidradii* nematodes treated with three components, Rehmannia (groundnut extract), Poria (Poria extract) and Ginseng (ginseng extract containing rare ginsenosides). Some genes that were up-regulated during JadeAging, such as CRP-1, GST-5, and GST-20, were also up-regulated in *Hidradenitis elegans* nematodes treated with Ginseng. Similarly, GST-4 was down-regulated in JadeAging and also in Poria and Rehmannia-treated *Cryptomeria hidradii* nematodes. On the other hand, some genes that were differentially expressed in JadeAging-treated *Cryptosporidium hidradii* nematodes, such as RSKS-1, SIP-1, PHI-62, DAF-12, and DAF-2, were not found to be significantly differentially expressed in *Cryptosporidium hidradii* nematodes treated with other components.

2) GO Enrichment

In transcriptomic analyses, studying the coordinated regulation of genes grouped according to their function can reveal changes in biological processes that are not apparent at the level of individual genes. GO enrichment analyses are a common approach that groups differentially regulated genes according to their annotated molecular functions. For this analysis, we used the more traditional significance cutoff of P<0.05 and a fold change cutoff of ±1.5. The results showed that *H. hidradii* nematodes treated with JadeAging, Ginseng, and Rehmannia were significantly enriched in GO entries at day 2, as summarized in Tables 9-11, whereas JadeAging-treated *H. hidradii* nematodes did not have a significant enrichment of GO entries at day 9, and Poria-treated *H. hidradii* nematodes had no GO entries enriched on both days 2 and 9.

TABLE 10

GO enrichment of Ginseng-treated
*Cryptobacterium hidradii* nematodes on day 2

| GO ID | Term | N | Up | Down | FDR-adjusted P-value | Elim pruning P-value |
|---|---|---|---|---|---|---|
| GO: 0045087 | innate immune response | 239 | 24 | 1 | 2.70E−09 | <1E−10 |
| GO: 0055114 | oxidation-reduction process | 632 | 35 | 5 | 2.70E−09 | <1E−10 |
| GO: 0042738 | exogenous drug catabolic process | 39 | 7 | 2 | 3.60E−05 | 3.40E−08 |
| GO: 0006805 | xenobiotic metabolic process | 48 | 7 | 2 | 1.60E−04 | 2.30E−07 |
| GO: 0006629 | lipid metabolic process | 473 | 24 | 0 | 1.96E−03 | 3.22E−03 |
| GO: 0009607 | response to biotic stimulus | 196 | 12 | 2 | 6.12E−03 | 3.17E−02 |
| GO: 0043207 | response to external biotic stimulus | 196 | 12 | 2 | 6.12E−03 | 3.17E−02 |
| GO: 0051707 | response to other organisms | 196 | 12 | 2 | 6.12E−03 | 3.17E−02 |
| GO: 0050829 | Defense response to Gram-negative bacterium | 97 | 8 | 1 | 2.14E−02 | 6.40E−05 |
| GO: 0097501 | Stress response to metal ion | 26 | 5 | 0 | 3.35E−02 | 2.73E−02 |

TABLE 11

Day 2 GO enrichment of Rehmannia-treated
*Cryptobacterium hidradii* nematodes

| GO ID | Term | N | Up | Down | FDR-adjusted P-value | Elim pruning P-value |
|---|---|---|---|---|---|---|
| GO: 0045087 | innate immune response | 239 | 4 | 13 | 3.60E−09 | <1E−10 |
| GO: 0050830 | Defense response to Gram-positive bacterium | 70 | 2 | 6 | 2.50E−05 | 4.80E−08 |
| GO: 0050829 | Defense response to Gram-negative bacterium | 97 | 2 | 4 | 4.02E−02 | 8.30E−05 |

JadeAging, Ginseng, and Rehmannia-treated *Cryptococcus hidradii* nematode samples showed GO enrichment associated with defense against Gram-negative bacteria and innate immune responses, where activation of innate immune responses was associated with increased longevity (Kumar et al., 2019). JadeAging and Ginseng-treated *Cryptococcus hidradii* nematode samples also showed GO

TABLE 9

GO enrichment of JadeAging-treated
*Cryptobacterium hidradii* nematodes on day 2

| GO ID | Term | N | Up | Down | FDR-adjusted P-value | Elim pruning P-value |
|---|---|---|---|---|---|---|
| GO: 0045087 | innate immune response | 239 | 6 | 3 | 1.80E-05 | 6.30E-09 |
| GO: 0042738 | exogenous drug catabolic process | 39 | 5 | 0 | 9.50E-05 | 6.00E-08 |
| GO: 0006805 | xenobiotic metabolic process | 48 | 5 | 0 | 0.00018 | 1.80E-07 |
| GO: 0055114 | oxidation-reduction process | 632 | 9 | 0 | 0.01284 | 2.00E-05 |
| GO: 0050829 | Defense response to Gram-negative bacterium | 97 | 3 | 1 | 0.04941 | 0.00012 | enrichment related to detoxification and metabolism, exogenous drug catabolic processes and xenobiotic metabolic processes. In addition, the samples of *Cryptobacterium hidradii* nematode treated by the samples to be tested all showed GO enrichment in redox processes, supporting their oxidative stress resistance.

3) Differential Gene Expression

We identified differential gene expression in day 2 and day 9 samples from all experimental groups (FIG. 14). Among them, Ginseng-treated *Cryptomeria hidradii* nematodes had the highest number on day 2 (326) and day 9 (812).

CONCLUSION

*Hidradenitis elegans* nematode was used as an animal model to explore the mechanism of action of JadeAging products against aging using mRNA sequencing. *Hidradenitis elegans* nematodes were treated with JadeAging, Ginseng, Poria, and Rehmannia, and then analyzed by RNA-Seq in the early and late stages of the life of *Hidradenitis elegans* nematodes. The results showed that JadeAging had a significant effect on the expression of genes related to nutrient sensing, stress-related pathways and redox processes.

GO enrichment analysis showed that JadeAging, Ginseng, Poria, and Rehmannia-treated *Cryptobacterium hidradii* nematodes showed GO enrichment for redox processes in vivo. In addition, JadeAging, Ginseng, and Rehmannia-treated samples showed GO enrichment associated with defense against Gram-negative bacteria and innate immune responses, which have previously been suggested to be associated with increased lifespan.

The total number of differentially expressed genes (DEGs) in the JadeAging, Ginseng, Poria, and Rehmannia test groups was characterized, with the highest number of differentially expressed genes (DEGs) in the Ginseng-treated samples, and the similarity of differential gene expression between the JadeAging and Ginseng groups, suggesting that their action mechanisms may overlap.

The foregoing description of the disclosed embodiments enables those skilled in the art to realize or use the present invention. Various modifications to these embodiments will be apparent to those skilled in the art, and the general principles defined herein may be realized in other embodiments without departing from the spirit or scope of the present invention. Accordingly, the present invention will not be limited to these embodiments shown herein, but will be subject to the broadest scope consistent with the principles and novel features disclosed herein.

What is claimed is:

1. A method for preparing ginseng extract rich in rare ginsenosides (GS), characterized in that it is prepared by the method of enzymatic hydrolysis and heat treatment, comprising:

(1) preparing ginseng stems and leaves extract dry powder or ginseng roots extract dry powder with water to form a substrate with a concentration of 10-20% (w/v), and adjusting a pH to 4.3-5.0;

(2) adding 2~5 U/g β-glucosidase for enzymatic hydrolysis under 40~60° C. for 3~5 h; after enzymatic hydrolysis; heating for 1~4 h at 115~132° C. and 70~200 kPa after the enzymatic hydrolysis;

(3) concentrating, under a temperature of 75~85° C. and a concentration pressure of −0.05~−0.09 Mpa, until a specific gravity is 1.1-1.2 g/L to obtain the concentrated solution; the temperature of the concentrated solution during the measuring of the specific gravity is 25° C.;

(4) subjecting the concentrated solution obtained in the step (3) to centrifugal spray drying with following conditions: inlet air temperature 135-160° C., outlet air temperature 80-100° C., centrifugal frequency 250-280 Hz, induced air frequency 50-60 Hz, and feed pump 10-40RPM.

2. The method for preparing ginseng extract rich in rare GS of claim 1, comprising:

(1) preparing ginseng stems and leaves extract dry powder or ginseng roots extract dry powder with water to form a substrate with a concentration of 15%, and adjusting a pH to 4.5;

(2) adding 3 U/g β-glucosidase for enzymatic hydrolysis under 50° C. for 4 h; after enzymatic hydrolysis; heating for 2 h at 115° C. and 70 kPa after the enzymatic hydrolysis;

(3) concentrating, under a temperature of 77° C. and a concentration pressure of −0.08 Mpa, until a specific gravity is 1.15 g/L to obtain the concentrated solution; the temperature of the concentrated solution during the measuring of the specific gravity is 25° C.;

(4) subjecting the concentrated solution obtained in the step (3) to centrifugal spray drying with following conditions: inlet air temperature 140° C., outlet air temperature 100° C., centrifugal frequency 280 Hz, induced air frequency 50 Hz, and feed pump 20RPM.

3. The method for preparing ginseng extract rich in rare ginsenosides of claim 1, characterized in that the ginseng stems and leaves extract dry powder is prepared as follows:

extracting by ethanol, an ethanol concentration is 70%, the ratio of the extracted material to liquid is 1:8, the number of extraction times is 2 times, and the time of each extraction is 2 hours, and an alcoholic extract is obtained;

concentrating the alcoholic extract under 65° C., and a concentration pressure of −0.06 Mpa until a specific gravity reaches 1.05 g/L, to obtain the concentrate; wherein a specific gravity measurement of the concentrate temperature is 25° C.; and centrifugal spray drying the concentrate under the conditions of: inlet temperature 140° C., outlet temperature 100° C., centrifugal frequency 280 Hz, induced air frequency 50 Hz and feed pump 20RPM.

4. The method for preparing ginseng extract rich in rare ginsenosides according to claim 1, characterized in that the ginseng roots extract dry powder is prepared as follows:

extracting by ethanol, an ethanol concentration is 60%, the ratio of the extracted material to liquid is 1:10, the number of extraction times is 3 times, and the time of each extraction is 3 hours, and an alcoholic extract is obtained;

concentrating the alcoholic extract under 65° C., and a concentration pressure of −0.06 Mpa until a specific gravity reaches 1.05 g/L, to obtain the concentrate; wherein a specific gravity measurement of the concentrate temperature is 25° C.; and centrifugal spray drying the concentrate under the conditions of: inlet temperature 140° C., outlet temperature 100° C., centrifugal frequency 280 Hz, induced air frequency 50 Hz and feed pump 20RPM.

5. The method for preparing ginseng extract rich in rare ginsenosides according to claim 3, characterized in that the ginseng stems and leaves extract enriched with rare ginsenosides is obtained; the proportion of rare ginsenosides in the ginseng stems and leaves extract is higher than or equal to 30%.

6. The method for preparing ginseng extract rich in rare ginsenosides according to claim 4, characterized in that the ginseng roots extract enriched with rare ginsenosides is obtained; the proportion of rare ginsenosides in the ginseng roots extract is higher than or equal to 15%.

\* \* \* \* \*